US008753861B2

(12) United States Patent
Cascao-Pereira et al.

(10) Patent No.: US 8,753,861 B2
(45) Date of Patent: *Jun. 17, 2014

(54) PROTEASE COMPRISING ONE OR MORE COMBINABLE MUTATIONS

(75) Inventors: Luis G. Cascao-Pereira, Redwood City, CA (US); David A. Estell, San Francisco, CA (US); James T. Kellis, Jr., San Carlos, CA (US)

(73) Assignee: Danisco US Inc., Palo Alto, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 13/128,854

(22) PCT Filed: Nov. 10, 2009

(86) PCT No.: PCT/US2009/063837
§ 371 (c)(1),
(2), (4) Date: Aug. 1, 2011

(87) PCT Pub. No.: WO2010/056653
PCT Pub. Date: May 20, 2010

(65) Prior Publication Data
US 2012/0003718 A1   Jan. 5, 2012

Related U.S. Application Data

(60) Provisional application No. 61/113,545, filed on Nov. 11, 2008, provisional application No. 61/218,802, filed on Jun. 19, 2009.

(51) Int. Cl.
*C12N 9/54* (2006.01)
*C12N 1/21* (2006.01)
(52) U.S. Cl.
USPC ............................ 435/222; 435/221; 435/264
(58) Field of Classification Search
CPC ................................. C12N 9/54; C12D 3/386
USPC .................................................. 435/222, 264
See application file for complete search history.

(56) References Cited

U.S. PATENT DOCUMENTS

| | | | |
|---|---|---|---|
| 4,246,612 A | 1/1981 | Berry et al. |
| 4,430,243 A | 2/1984 | Bragg |
| 4,435,307 A | 3/1984 | Barbesgaard et al. |
| 4,683,195 A | 7/1987 | Mullis et al. |
| 4,683,202 A | 7/1987 | Mullis |
| 4,810,410 A | 3/1989 | Diakun et al. |
| 4,965,188 A | 10/1990 | Mullis et al. |
| 4,977,252 A | 12/1990 | Chiu |
| 5,024,943 A | 6/1991 | Van Ee |
| 5,227,084 A | 7/1993 | Martens et al. |
| RE34,606 E | 5/1994 | Estell et al. |
| 5,340,735 A | 8/1994 | Christianson et al. |
| 5,354,559 A | 10/1994 | Morehouse |
| 5,427,936 A | 6/1995 | Moeller et al. |
| 5,486,303 A | 1/1996 | Capeci et al. |
| 5,489,392 A | 2/1996 | Capeci et al. |
| 5,500,364 A | 3/1996 | Christianson et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,646,101 A | 7/1997 | MacBeath |
| 5,686,014 A | 11/1997 | Baillely et al. |
| 5,691,297 A | 11/1997 | Nassano et al. |
| 5,695,679 A | 12/1997 | Christie et al. |
| 5,698,504 A | 12/1997 | Christie et al. |
| 5,700,676 A | 12/1997 | Bott et al. |
| 5,705,464 A | 1/1998 | Scheper et al. |
| 5,710,115 A | 1/1998 | Patel et al. |
| 5,795,855 A | 8/1998 | Schneider et al. |
| 5,801,039 A | 9/1998 | Maurer et al. |
| 5,855,625 A | 1/1999 | Maurer et al. |
| 5,874,276 A | 2/1999 | Fowler et al. |
| 5,879,584 A | 3/1999 | Bianchetti et al. |
| 5,935,826 A | 8/1999 | Blue et al. |
| 5,955,340 A | 9/1999 | Bott et al. |
| 6,225,464 B1 | 5/2001 | Hiler, II et al. |
| 6,271,012 B1 | 8/2001 | Van Eekelen et al. |
| 6,306,812 B1 | 10/2001 | Perkins et al. |
| 6,312,936 B1 | 11/2001 | Poulose et al. |

(Continued)

FOREIGN PATENT DOCUMENTS

| | | |
|---|---|---|
| CA | 2162459 | 11/1994 |
| CA | 2162460 | 11/1994 |

(Continued)

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
U.S. Appl. No. 11/583,334, filed Oct. 19, 2006, Wolfgang et al.
U.S. Appl. No. 10/576,331, filed Jul. 18, 2007, Jones et al.
U.S. Appl. No. 11/825,731, filed Apr. 17, 2008, Augustinus et al.
U.S. Appl. No. 11/581,102, filed Nov. 27, 2008, Shaw et al.

(Continued)

*Primary Examiner* — Tekchand Saidha
*Assistant Examiner* — Md. Younus Meah
(74) *Attorney, Agent, or Firm* — Danisco US Inc.

(57) ABSTRACT

The present invention provides engineered protease variants. In particular, the protease variants comprise combinable mutations at selected surface positions that affect the charge and/or hydrophobicity of the enzyme to enhance at least one desired property of the resulting variant enzyme in a chosen application. Compositions comprising the protease variants, and methods for using the same are also provided.

15 Claims, 4 Drawing Sheets

(56) References Cited

U.S. PATENT DOCUMENTS

| | | |
|---|---|---|
| 6,326,348 B1 | 12/2001 | Vinson et al. |
| 6,376,450 B1 | 4/2002 | Ghosh et al. |
| 6,440,991 B1 | 8/2002 | Zhu et al. |
| 6,472,184 B1 | 10/2002 | Hegemann |
| 6,482,628 B1 | 11/2002 | Poulose et al. |
| 6,509,021 B1 | 1/2003 | Weiss et al. |
| 6,566,114 B1 | 5/2003 | Kauppinen et al. |
| 6,582,914 B1 | 6/2003 | Caldwell et al. |
| 6,586,223 B1 | 7/2003 | Sikorski et al. |
| 6,599,730 B1 | 7/2003 | Brode, III et al. |
| 6,602,842 B2 | 8/2003 | Cuperus et al. |
| 6,605,458 B1 | 8/2003 | Hansen et al. |
| 6,610,642 B2 | 8/2003 | Ghosh et al. |
| 6,773,907 B2 | 8/2004 | Hansen et al. |
| 6,946,128 B1 | 9/2005 | Rubingh et al. |
| 8,224,578 B2 | 7/2012 | Raab et al. |
| 2005/0221461 A1 | 10/2005 | Poulose et al. |
| 2005/0239185 A1* | 10/2005 | Hansen et al. .................. 435/183 |
| 2008/0090747 A1 | 4/2008 | Augustinus et al. |
| 2009/0233831 A1 | 9/2009 | Souter |
| 2011/0237487 A1 | 9/2011 | Souter et al. |
| 2011/0251073 A1 | 10/2011 | Cascao-Pereira et al. |
| 2011/0256610 A1 | 10/2011 | Alekseyev et al. |
| 2012/0003718 A1 | 1/2012 | Cascao-Pereira et al. |
| 2012/0067373 A1 | 3/2012 | Souter et al. |

FOREIGN PATENT DOCUMENTS

| | | |
|---|---|---|
| EP | 0 200 362 | 11/1986 |
| EP | 0 201 184 | 11/1986 |
| EP | 0 214 761 | 3/1987 |
| EP | 0 218 272 | 4/1987 |
| EP | 0 238 023 | 9/1987 |
| EP | 0 258 068 | 3/1988 |
| EP | 0 305 2161 | 3/1989 |
| EP | 0 331 376 | 9/1989 |
| EP | 0 342 177 | 11/1989 |
| EP | 0 495 257 | 7/1992 |
| EP | 2 100 949 | 9/2009 |
| GB | 1296839 | 11/1972 |
| GB | 1372034 | 10/1974 |
| JP | 64-074992 | 3/1989 |
| WO | WO 88/09367 | 12/1988 |
| WO | WO 89/06270 | 7/1989 |
| WO | WO 90/09446 | 8/1990 |
| WO | WO 92/21760 | 12/1992 |
| WO | WO 94/12621 | 6/1994 |
| WO | WO 95/23221 | 8/1995 |
| WO | WO 96/34935 | 11/1996 |
| WO | WO 97/11151 | 3/1997 |
| WO | WO 98/55634 | 12/1998 |
| WO | WO 99/06521 | 2/1999 |
| WO | WO 99/34011 | 7/1999 |
| WO | WO 99/53038 | 10/1999 |
| WO | WO 00/32601 | 6/2000 |
| WO | WO 00/71686 | 11/2000 |
| WO | WO 01/07577 | 2/2001 |
| WO | WO 02/14490 | 2/2002 |
| WO | WO 02/40997 | 5/2002 |
| WO | WO 03/006602 | 1/2003 |
| WO | WO 2005/056782 | 6/2005 |
| WO | WO 2007/044993 | 4/2007 |
| WO | WO 2007/145964 | 12/2007 |
| WO | WO 2008/010925 | 1/2008 |
| WO | WO 2009/149144 | 12/2009 |
| WO | WO 2009/149200 | 12/2009 |
| WO | WO 2011/036263 | 3/2011 |

OTHER PUBLICATIONS

Altschul, S.F. et al. "Local alignment statistics." *Methods Enzymol* 266:460-80, 1996.
Altschul, S.F. et al. "Basic local alignment search tool." *J. Mol. Biol* 215(3):403-410, 1990.
Bolivar, F. et al. "Construction and characterization of new cloning vehicles. II. A multipurpose cloning system." *Gene* 2(2) :95-113, 1977.
Bryan, P.N., "Protein engineering of subtilisin." *Biochimica et Biophysica Acta* 1543(2): 203-222 (2000).
Dartois, V. et al. "Cloning, nucleotide sequence and expression in *Escherichia coli* of a lipase gene from *Bacillus subtilis* 168." *Biochimica et Biophysica Acta* 1131(3):253-260, 1992.
Delmar, E.G. et al. "A sensitive new substrate for chymotrypsin." *Analytical Biochemistry* 99(2):316-320, 1979.
Devereux, P. et al. "A comprehensive set of sequence analysis programs for the VAX." *Nucl. Acids Res* 12:387-395, 1984.
Dynan, W.S. et al. "Control of eukaryotic messenger RNA synthesis by sequence-specific DNA-binding proteins." *Nature* 316(6031):774-778, 1985.
Estell, D.A. et al. "Site-directed mutagenesis of the active site of Subtilisin BPN." In *The World Biotech Report 1984: The Proceedings of Biotech 84*, USA, Pinner, UK: Online Publications, pp. 181-187, 1984.
Feng, D.F. et al. "Progressive sequence alignment as a prerequisite to correct phylogenetic trees." *J. Mol. Evol* 25(4):351-360, 1987.
Ferrari, E. et al. "Genetics." In *Bacillus*, Biotechnology Handbooks, No. 2, Ed. C.R. Harwood. New York: Plenum Press, pp. 57-72, 1989.
Haas, M.J. et al. "Cloning, expression and characterization of a cDNA encoding a lipase from *Rhizopus delemar*." *Gene* 109(1):107-113, 1991.
Heinz, D.W. et al. "Changing the inhibitory specificity and function of the proteinase inhibitor eglin c by site-directed mutagenesis: functional and structural investigation." *Biochemistry* 31(37):8755-8766, 1992.
Higgins, D.G. et al. "Fast and sensitive multiple alignment sequence on a microcomputer." *CABIOS* 5:151-153, 1989.
Horinouchi, S. et al. "Nucleotide sequence and functional map of pC194, a plasmid that specifies inducible chloramphenicol resistance . . . " *J. Bacteriol.* 150(2):815-825, 1982.
Kalisz, H.M. "Microbial proteinases." *Advances in Biochemical Engineering/Biotechnology* 36:1-65, 1988.
Karlin, S. et al. "Applications and statistics for multiple high-scoring segments in molecular sequences." *Proc. Natl. Acad. Sci.* USA 90(12):5873-7, 1993.
Kato, R. et al. "Novel Strategy for Protein Exploration: High-throughput Screening Assisted with Fuzzy Neural Network." *Journal of Molecular Biology* 351(3):683-692, 2005.
Kugimiya, W. et al. "Cloning and sequence analysis of cDNA encoding *Rhizopus niveus* lipase." *Bioscience, Biotechnology, and Biochemistry* 56(5) :716-9, 1992.
McKenzie, T. et al. "The nucleotide sequence of pUB110: some salient features in relation to replication and its regulation." *Plasmid* 15(2):93-103, 1986.
Needleman, S.B. et al. "A general method applicable to the search for similarities in the amino acid sequence of two proteins." *J. Mol. Biol* 48(3):443-53, 1970.
Neidhardt, F.C. et al. "Culture Medium for Enterobacteria." *J. Bacteriol.* 119(3):736-747, 1974.
Pearson, W.R. et al. "Improved Tools for Biological Sequence Comparison." *Proc. Natl. Acad. Sci.* USA 85(8):2444-2448, 1988.
Pierce, N.A. et al. "Protein design is NP-hard." *Protein Engineering* 15(10):779-82, 2002.
Rawlings, N.D. et al. "Evolutionary families of peptidases . . . " *Biochem. J.* 290(1):205-218, 1993.
Rawlings, N.D. et al. "MEROPS: the peptidase database." *Nucl. Acids Res.* 34(Suppl. 1):D270-272, 2006.
Reetz, M.T. et al. "Expanding the Range of Substrate Acceptance of Enzymes: Combinatorial Active-Site Saturation Test13." *Angewandte Chemie International Edition* 44(27):4192-4196, 2005.
Sandberg, W.S. et al. "Engineering multiple properties of a protein by combinatorial mutagenesis." *Proc. Natl. Acad. Sci.* U.S.A 90(18):8367-71, 1993.
Shimada, Y. et al. "cDNA Molecular Cloning of *Geotrichum candidum* Lipase." *J Biochem* 106(3):383-388, 1989.

(56) References Cited

OTHER PUBLICATIONS

Smith, T.F. et al. "Comparison of biosequences." *Adv. Appl. Math* 2:482-489, 1981.

Wells, J A et al. "Cassette mutagenesis: an efficient method for generation of multiple mutations at defined sites." *Gene* 34(2-3):315-23, 1985.

Wells, J.A. et al. "Cloning, sequencing, and secretion of *Bacillus amyloliquefaciens* subtillisin in *Bacillus subtilis*." *Nucl. Acids Res.* 11(22):7911-7925, 1983.

Yamaguchi, S. et al. "Cloning and structure of the mono- and diacylglycerol lipase-encoding gene from *Penicillium camembertii* U-150." *Gene* 103(1):61-7, 1991.

International Search Report and the Written Opinion of the International Searching Authority for International Patent Application No. PCT/US2009/063808 dated Aug. 23, 2010.

International Search Report and the Written Opinion of the International Searching Authority for International Patent Application No. PCT/US2009/063837 dated Jul. 27, 2010.

Partial European Search Report for EP Application No. 13150801.2 dated Apr. 9, 2013.

* cited by examiner

```
            1         10        20        30        40        50
BPN'    AQSVPYGVSQIKAPALHSQGYTGSNVKVAVIDSGIDSSHPDLKVAGGASM
FNA     AQSVPYGVSQIKAPALHSQGYTGSNVKVAVIDSGIDSSHPDLKVAGGASM
GG36    AQSVPWGISRVQAPAAHNRGLTGSGVKVAVLDTGI*STHPDLNIRGGASF 51        60        70        80        90        100
BPN'    VPSETNPFQDNNSHGTHVAGTVAALNNSIGVLGVAPSASLYAVKVLGADG
FNA     VPSETNPFQDNNSHGTHVAGTVAALNNSIGVLGVAPSASLYAVKVLGADG
GG36    VPGEPST*QDGNGHGTHVAGTIAALNNSIGVLGVAPSAELYAVKVLGASG 101       110       120       130       140       150
BPN'    SGQYSWIINGIEWAIANNMDVINMSLGGPSGSAALKAAVDKAVASGVVVV
FNA     SGQYSWIINGIEWAIANNMDVINMSLGGPSGSAALKAAVDKAVASGVVVV
GG36    SGSVSSIAQGLEWAGNNGMHVANLSLGSPSPSATLEQAVNSATSRGVLVV 151       160       170       180       190       200
BPN'    AAAGNEGTSGSSSTVGYPGKYPSVIAVGAVDSSNQRASFSSVGPELDVMA
FNA     AAAGNEGTSGSSSTVGYPGKYPSVIAVGAVDSSNQRASFSSVGPELDVMA
GG36    AASGNSGAGS****ISYPARYANAMAVGATDQNNNRASFSQYGAGLDIVA 201       210       220       230       240       250
BPN'    PGVSIQSTYPGNKYGAYNGTSMASPHVAGAAALILSKHPNWTNTQVRSSL
FNA     PGVSIQSTLPGNKYGALNGTSMASPHVAGAAALILSKHPNWTNTQVRSSL
GG36    PGVNVQSTYPGSTYASLNGTSMATPHVAGAAALVKQKNPSWSNVQIRNHL 251       260       270
BPN'    ENTTTKLGDSFYYGKGLINVQAAAQ    (SEQ ID NO:1)
FNA     ENTTTKLGDSFYYGKGLINVQAAAQ    (SEQ ID NO:7)
GG36    KNTATSLGSTNLYGSGLVNAEAATR    (SEQ ID NO:4)
```

*FIG. 1*

| Matrix of Charge Change at pH 8.6 by Amino Acid Substitution | | | | | | | | | | | | | | | | | | | |
|---|---|---|---|---|---|---|---|---|---|---|---|---|---|---|---|---|---|---|---|
| Amino Acid | A | C | D | E | F | G | H | I | K | L | M | N | P | Q | R | S | T | V | W | Y |
| A | 0 | 0 | -1 | -1 | 0 | 0 | 0 | 0 | 1 | 0 | 0 | 0 | 0 | 0 | 1 | 0 | 0 | 0 | 0 | 0 |
| C | 0 | 0 | -1 | -1 | 0 | 0 | 0 | 0 | 1 | 0 | 0 | 0 | 0 | 0 | 1 | 0 | 0 | 0 | 0 | 0 |
| D | 1 | 1 | 0 | 0 | 1 | 1 | 1 | 1 | 2 | 1 | 1 | 1 | 1 | 1 | 2 | 1 | 1 | 1 | 1 | 1 |
| E | 1 | 1 | 0 | 0 | 1 | 1 | 1 | 1 | 2 | 1 | 1 | 1 | 1 | 1 | 2 | 1 | 1 | 1 | 1 | 1 |
| F | 0 | 0 | -1 | -1 | 0 | 0 | 0 | 0 | 1 | 0 | 0 | 0 | 0 | 0 | 1 | 0 | 0 | 0 | 0 | 0 |
| G | 0 | 0 | -1 | -1 | 0 | 0 | 0 | 0 | 1 | 0 | 0 | 0 | 0 | 0 | 1 | 0 | 0 | 0 | 0 | 0 |
| H | 0 | 0 | -1 | -1 | 0 | 0 | 0 | 0 | 1 | 0 | 0 | 0 | 0 | 0 | 1 | 0 | 0 | 0 | 0 | 0 |
| I | 0 | 0 | -1 | -1 | 0 | 0 | 0 | 0 | 1 | 0 | 0 | 0 | 0 | 0 | 1 | 0 | 0 | 0 | 0 | 0 |
| K | -1 | -1 | -2 | -2 | -1 | -1 | -1 | -1 | 0 | -1 | -1 | -1 | -1 | -1 | 0 | -1 | -1 | -1 | -1 | -1 |
| L | 0 | 0 | -1 | -1 | 0 | 0 | 0 | 0 | 1 | 0 | 0 | 0 | 0 | 0 | 1 | 0 | 0 | 0 | 0 | 0 |
| M | 0 | 0 | -1 | -1 | 0 | 0 | 0 | 0 | 1 | 0 | 0 | 0 | 0 | 0 | 1 | 0 | 0 | 0 | 0 | 0 |
| N | 0 | 0 | -1 | -1 | 0 | 0 | 0 | 0 | 1 | 0 | 0 | 0 | 0 | 0 | 1 | 0 | 0 | 0 | 0 | 0 |
| P | 0 | 0 | -1 | -1 | 0 | 0 | 0 | 0 | 1 | 0 | 0 | 0 | 0 | 0 | 1 | 0 | 0 | 0 | 0 | 0 |
| Q | 0 | 0 | -1 | -1 | 0 | 0 | 0 | 0 | 1 | 0 | 0 | 0 | 0 | 0 | 1 | 0 | 0 | 0 | 0 | 0 |
| R | -1 | -1 | -2 | -2 | -1 | -1 | -1 | -1 | 0 | -1 | -1 | -1 | -1 | -1 | 0 | -1 | -1 | -1 | -1 | -1 |
| S | 0 | 0 | -1 | -1 | 0 | 0 | 0 | 0 | 1 | 0 | 0 | 0 | 0 | 0 | 1 | 0 | 0 | 0 | 0 | 0 |
| T | 0 | 0 | -1 | -1 | 0 | 0 | 0 | 0 | 1 | 0 | 0 | 0 | 0 | 0 | 1 | 0 | 0 | 0 | 0 | 0 |
| V | 0 | 0 | -1 | -1 | 0 | 0 | 0 | 0 | 1 | 0 | 0 | 0 | 0 | 0 | 1 | 0 | 0 | 0 | 0 | 0 |
| W | 0 | 0 | -1 | -1 | 0 | 0 | 0 | 0 | 1 | 0 | 0 | 0 | 0 | 0 | 1 | 0 | 0 | 0 | 0 | 0 |
| Y | 0 | 0 | -1 | -1 | 0 | 0 | 0 | 0 | 1 | 0 | 0 | 0 | 0 | 0 | 1 | 0 | 0 | 0 | 0 | 0 |

*FIG. 2*

| Matrix of Hydropathicity Changes by Amino Acid Substitution (Kyte-Doolittle) | | | | | | | | | | | | | | | | | | | |
|---|---|---|---|---|---|---|---|---|---|---|---|---|---|---|---|---|---|---|---|
| Amino Acid | A | C | D | E | F | G | H | I | K | L | M | N | P | Q | R | S | T | V | W | Y |
| A | 0.0 | 0.7 | -5.3 | -5.3 | 1.0 | -2.2 | -5.0 | 2.7 | -5.7 | 2.0 | 0.1 | -5.3 | -3.4 | -5.3 | -6.3 | -2.6 | -2.5 | 2.4 | -2.7 | -3.1 |
| C | -0.7 | 0.0 | -6.0 | -6.0 | 0.3 | -2.9 | -5.7 | 2.0 | -6.4 | 1.3 | -0.6 | -6.0 | -4.1 | -6.0 | -7.0 | -3.3 | -3.2 | 1.7 | -3.4 | -3.8 |
| D | 5.3 | 6.0 | 0.0 | 0.0 | 6.3 | 3.1 | 0.3 | 8.0 | -0.4 | 7.3 | 5.4 | 0.0 | 1.9 | 0.0 | -1.0 | 2.7 | 2.8 | 7.7 | 2.6 | 2.2 |
| E | 5.3 | 6.0 | 0.0 | 0.0 | 6.3 | 3.1 | 0.3 | 8.0 | -0.4 | 7.3 | 5.4 | 0.0 | 1.9 | 0.0 | -1.0 | 2.7 | 2.8 | 7.7 | 2.6 | 2.2 |
| F | -1.0 | -0.3 | -6.3 | -6.3 | 0.0 | -3.2 | -6.0 | 1.7 | -6.7 | 1.0 | -0.9 | -6.3 | -4.4 | -6.3 | -7.3 | -3.6 | -3.5 | 1.4 | -3.7 | -4.1 |
| G | 2.2 | 2.9 | -3.1 | -3.1 | 3.2 | 0.0 | -2.8 | 4.9 | -3.5 | 4.2 | 2.3 | -3.1 | -1.2 | -3.1 | -4.1 | -0.4 | -0.3 | 4.6 | -0.5 | -0.9 |
| H | 5.0 | 5.7 | -0.3 | -0.3 | 6.0 | 2.8 | 0.0 | 7.7 | -0.7 | 7.0 | 5.1 | -0.3 | 1.6 | -0.3 | -1.3 | 2.4 | 2.5 | 7.4 | 2.3 | 1.9 |
| I | -2.7 | -2.0 | -8.0 | -8.0 | -1.7 | -4.9 | -7.7 | 0.0 | -8.4 | -0.7 | -2.6 | -8.0 | -6.1 | -8.0 | -9.0 | -5.3 | -5.2 | -0.3 | -5.4 | -5.8 |
| K | 5.7 | 6.4 | 0.4 | 0.4 | 6.7 | 3.5 | 0.7 | 8.4 | 0.0 | 7.7 | 5.8 | 0.4 | 2.3 | 0.4 | -0.6 | 3.1 | 3.2 | 8.1 | 3.0 | 2.6 |
| L | -2.0 | -1.3 | -7.3 | -7.3 | -1.0 | -4.2 | -7.0 | 0.7 | -7.7 | 0.0 | -1.9 | -7.3 | -5.4 | -7.3 | -8.3 | -4.6 | -4.5 | 0.4 | -4.7 | -5.1 |
| M | -0.1 | 0.6 | -5.4 | -5.4 | 0.9 | -2.3 | -5.1 | 2.6 | -5.8 | 1.9 | 0.0 | -5.4 | -3.5 | -5.4 | -6.4 | -2.7 | -2.6 | 2.3 | -2.8 | -3.2 |
| N | 5.3 | 6.0 | 0.0 | 0.0 | 6.3 | 3.1 | 0.3 | 8.0 | -0.4 | 7.3 | 5.4 | 0.0 | 1.9 | 0.0 | -1.0 | 2.7 | 2.8 | 7.7 | 2.6 | 2.2 |
| P | 3.4 | 4.1 | -1.9 | -1.9 | 4.4 | 1.2 | -1.6 | 6.1 | -2.3 | 5.4 | 3.5 | -1.9 | 0.0 | -1.9 | -2.9 | 0.8 | 0.9 | 5.8 | 0.7 | 0.3 |
| Q | 5.3 | 6.0 | 0.0 | 0.0 | 6.3 | 3.1 | 0.3 | 8.0 | -0.4 | 7.3 | 5.4 | 0.0 | 1.9 | 0.0 | -1.0 | 2.7 | 2.8 | 7.7 | 2.6 | 2.2 |
| R | 6.3 | 7.0 | 1.0 | 1.0 | 7.3 | 4.1 | 1.3 | 9.0 | 0.6 | 8.3 | 6.4 | 1.0 | 2.9 | 1.0 | 0.0 | 3.7 | 3.8 | 8.7 | 3.6 | 3.2 |
| S | 2.6 | 3.3 | -2.7 | -2.7 | 3.6 | 0.4 | -2.4 | 5.3 | -3.1 | 4.6 | 2.7 | -2.7 | -0.8 | -2.7 | -3.7 | 0.0 | 0.1 | 5.0 | -0.1 | -0.5 |
| T | 2.5 | 3.2 | -2.8 | -2.8 | 3.5 | 0.3 | -2.5 | 5.2 | -3.2 | 4.5 | 2.6 | -2.8 | -0.9 | -2.8 | -3.8 | -0.1 | 0.0 | 4.9 | -0.2 | -0.6 |
| V | -2.4 | -1.7 | -7.7 | -7.7 | -1.4 | -4.6 | -7.4 | 0.3 | -8.1 | -0.4 | -2.3 | -7.7 | -5.8 | -7.7 | -8.7 | -5.0 | -4.9 | 0.0 | -5.1 | -5.5 |
| W | 2.7 | 3.4 | -2.6 | -2.6 | 3.7 | 0.5 | -2.3 | 5.4 | -3.0 | 4.7 | 2.8 | -2.6 | -0.7 | -2.6 | -3.6 | 0.1 | 0.2 | 5.1 | 0.0 | -0.4 |
| Y | 3.1 | 3.8 | -2.2 | -2.2 | 4.1 | 0.9 | -1.9 | 5.8 | -2.6 | 5.1 | 3.2 | -2.2 | -0.3 | -2.2 | -3.2 | 0.5 | 0.6 | 5.5 | 0.4 | 0.0 |

PROTEASE COMPRISING ONE OR MORE COMBINABLE MUTATIONS

The present application is a U.S. National Stage application of International Application No. PCT/US2009/063837, filed on Nov. 10, 2009, which claims the benefit of U.S. Provisional Application. No. 61/218,802, filed on Jun. 19, 2009 and U.S. Provisional Application. No. 61/113,545 filed on Nov. 11, 2008, each of which are herein incorporated by reference.

SEQUENCE LISTING

The sequence listing submitted via EFS, in compliance with 37 C.F.R. §1.52(e), is incorporated herein by reference. The sequence listing text file submitted via EFS contains the file "31065-B-SEQLIST.txt" created on Jun. 20, 2011, which is 19,239 bytes in size.

FIELD OF THE INVENTION

The present invention provides engineered protease variants. In particular, the protease variants comprise combinable mutations at selected surface positions that affect the charge and/or hydrophobicity of the enzyme to enhance at least one desired property of the resulting variant enzyme in a chosen application. Compositions comprising the protease variants, and methods for using the same are also provided.

BACKGROUND OF THE INVENTION

Serine proteases are a subgroup of carbonyl hydrolases comprising a diverse class of enzymes having a wide range of specificities and biological functions. Much research has been conducted on the subtilisins, due largely to their usefulness in cleaning and feed applications. Additional work has been focused on the adverse environmental conditions (e.g., exposure to oxidative agents, chelating agents, extremes of temperature and/or pH) that can diminish the functionality of these enzymes in various applications. Nonetheless, there remains a need in the art for enzyme systems that are able to resist these adverse conditions and retain or have improved activity over those currently known in the art.

SUMMARY OF THE INVENTION

The present invention provides engineered protease variants. In particular, the protease variants comprise combinable mutations at selected surface positions that affect the charge and/or hydrophobicity of the enzyme to enhance at least one desired property of the resulting variant enzyme in a chosen application. Compositions comprising the protease variants, and methods for using the same are also provided.

In one embodiment, the protease variant is the mature form of an isolated subtilisin variant of a *Bacillus* subtilisin that has proteolytic activity and comprises a substitution two or more positions selected from positions 24, 45, 101, 109, 118, 213 and 217, wherein the positions are numbered by correspondence with the amino acid sequence of *B. amyloliquefaciens* subtilisin BPN' set forth as SEQ ID NO:1.

In another embodiment, the protease variant is the mature form of an isolated subtilisin variant of a *Bacillus* subtilisin that has proteolytic activity and comprises a substitution two or more positions selected from positions 24, 45, 101, 109, 118, 213 and 217, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5.

In another embodiment, the protease variant is the mature form of an isolated subtilisin variant of *Bacillus* subtilisin GG36 that has proteolytic activity and comprises two or more substitutions at two or more positions selected from S24Q, S24E, S24L, S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions are numbered by correspondence with the amino acid sequence of *B. amyloliquefaciens* subtilisin BPN' set forth as SEQ ID NO:1.

In another embodiment, the protease variant is the mature form of an isolated subtilisin variant of *Bacillus* subtilisin GG36 that has proteolytic activity and comprises two or more substitutions at two or more positions selected from : S24Q, S24E, S24L, S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5.

In another embodiment, the protease variant is the mature form of an isolated subtilisin variant of *Bacillus* subtilisin FNA that has proteolytic activity and comprises two or more substitutions at two or more positions selected from S24Q, S24E, S24L, S24R, A45Q, A45E, A45L, A45R, S101Q, S101E, S101L, S101R, N109Q, N109E, N109L, N109R, K213Q, K213E, K213L, K213R, L217Q, and L217E, wherein the positions are numbered by correspondence with the amino acid sequence of *B. amyloliquefaciens* subtilisin BPN' set forth as SEQ ID NO:1.

In another embodiment, the protease variant is the mature form of an isolated subtilisin variant of *Bacillus* subtilisin FNA that has proteolytic activity and comprises two or more substitutions at two or more positions selected from S24Q, S24E, S24L, S24R, A45Q, A45E, A45L, A45R, S101Q, S101E, S101L, S101R, N109Q, N109E, N109L, N109R, K213Q, K213E, K213L, K213R, L217Q, and L217E, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5.

In another embodiment, the protease variant is the mature form of an isolated subtilisin variant of a *Bacillus* subtilisin GG36 that has proteolytic activity and comprises a combination of substitutions selected from S24Q-R45Q-S101Q-G118Q-T213Q, R45Q-S101Q-G118Q-T213Q, S101Q-G118Q-T213Q, G118Q-T213Q, S24E-R45Q-S101Q-G118Q-T213Q, S24E-R45E-S101Q-G118Q-T213Q, S24E-R45E-S101E-G118Q-T213Q, S24E-R45E-S101E-Q109E-G118Q-T213Q, S24E-R45E-S101E-Q109E-G118E-T213Q, S24E-R45E-S101E-Q109E-G118E-T213E, S24L-R45Q-S101Q-G118Q-T213Q, S24L-R45L-S101Q-G118Q-T213Q, S24L-R45L-S101L-G118Q-T213Q, S24L-R45L-S101L-Q109L-G118Q-T213Q, S24L-R45L-S101L-Q109L-G118L-T213Q, S24L-R45L-S101L-Q109L-G118L-T213L, S24R-R45Q-S101Q-G118Q-T213Q, S24R-S101Q-G118Q-T213Q, S24R-S101R-G118Q-T213Q, S24R-S101R-Q109R-G118Q-T213Q, S24R-S101R-Q109R-G118R-T213Q, S24R-S101R-Q109R-G118R-T213R, S24E-

S101R-Q109R-G118R-T213R, S24E-R45E-S101R-Q109R-G118R-T213R, S24E-R45E-S101E-Q109R-G118R-T213R, S24E-R45E-S101E-Q109E-G118R-T213R, S24E-R45E-S101E-Q109E-G118E-T213R, S24E-R45E-S101E-Q109E-G118E-T213E, S24Q-R45Q-S101Q-G118Q-T213Q-L217Q, and S24Q-R45Q-S101Q-G118Q-T213Q-L217E, wherein the positions are numbered by correspondence with the amino acid sequence of *B. amyloliquefaciens* subtilisin BPN' set forth as SEQ ID NO:1

In another embodiment. the protease variant is the mature form of an isolated subtilisin variant of a *Bacillus* subtilisin GG36 that has proteolytic activity and comprises the substitution T213Q, wherein said position is numbered by correspondence with the amino acid sequence of *B. amyloliquefaciens* subtilisin BPN' set forth as SEQ ID NO:1.

In another embodiment. the protease variant is the mature form of an isolated subtilisin variant of a *Bacillus* subtilisin FNA that has proteolytic activity and a combination of substitutions selected from S24Q-A45Q-S101Q-N109Q-N118Q-K213Q, A45Q-S101Q-N109Q-N118Q-K213Q, S101Q-N109Q-N118Q-K213Q, N109Q-N118Q-K213Q, N118Q-K213Q, S24E-A45Q-S101Q-N109Q-N118Q-K213Q, S24E-A45E-S101Q-N109Q-N118Q-K213Q, S24E-A45E-S101E-N109Q-N118Q-K213Q, S24E-A45E-S101E-N109E-N118Q-K213Q, S24E-A45E-S101E-N109E-N118E-K213Q, S24E-A45E-S101E-N109E-N118E-K213E, S24L-A45Q-S101Q-N109Q-N118Q-K213Q, S24L-A45L-S101Q-N109Q-N118Q-K213Q, S24L-A45L-S101L-N109Q-N118Q-K213Q, S24L-A45L-S101L-N109L-N118Q-K213Q, S24L-A45L-S101L-N109L-N118L-K213Q, S24L-A45L-S101L-N109L-N118L-K213L, S24R-A45Q-S101Q-N109Q-N118Q-K213Q, S24R-A45R-S101Q-N109Q-N118Q-K213Q, S24R-A45R-S101R-N109Q-N118Q-K213Q, S24R-A45R-S101R-N109R-N118Q-K213Q, S24R-A45R-S101R-N109R-N118R-K213Q, S24R-A45R-S101R-N109R-N118R-K213R, S24E-A45R-S101R-N109R-N118R-K213R, S24E-A45E-S101R-N109R-N118R-K213R, S24E-A45E-S101E-N109R-N118R-K213R, S24E-A45E-S101E-N109E-N118R-K213R, S24E-A45E-S101E-N109E-N118E-K213R, S24E-A45E-S101E-N109E-N118E-K213E, S24Q-A45Q-S101Q-N109Q-N118Q-K213Q-L217Q, and S24Q-A45Q-S101Q-N109Q-N118Q-K213Q-L217E, wherein the positions correspond to the positions of BPN' subtilisin of SEQ ID NO:1.

In another embodiment. the protease variant is the mature form of an isolated subtilisin variant of a *Bacillus* subtilisin FNA that has proteolytic activity and comprises the substitution K213Q, wherein said position is numbered by correspondence with the amino acid sequence of *B. amyloliquefaciens* subtilisin BPN' set forth as SEQ ID NO:1.

In another embodiment, the invention provides an isolated nucleic acid that encodes any one of the protease variants described above.

In another embodiment, the invention provides an expression vector that comprises an isolated nucleic acid that encodes any one of the protease variants described above.

In another embodiment, the invention provides a host cell that comprises an expression vector, which in turn comprises an isolated nucleic acid that encodes any one of the protease variants described above.

In another embodiment, the invention provides a cleaning composition that comprises at least one protease variant that is the mature form of an isolated subtilisin variant of a *Bacillus* subtilisin that has proteolytic activity and comprises a substitution two or more positions selected from positions 24, 45, 101, 109, 118, 213 and 217, wherein the positions are numbered by correspondence with the amino acid sequence of *B. amyloliquefaciens* subtilisin BPN' set forth as SEQ ID NO:1. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin that has proteolytic activity and comprises a substitution two or more positions selected from positions 24, 45, 101, 109, 118, 213 and 217, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of *Bacillus* subtilisin GG36 that has proteolytic activity and comprises two or more substitutions at two or more positions selected from S24Q, S24E, S24L,S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions are numbered by correspondence with the amino acid sequence of *B. amyloliquefaciens* subtilisin BPN' set forth as SEQ ID NO:1. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of *Bacillus* subtilisin GG36 that has proteolytic activity and comprises two or more substitutions at two or more positions selected from : S24Q, S24E, S24L,S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of *Bacillus* subtilisin FNA that has proteolytic activity and comprises two or more substitutions at two or more positions selected from S24Q, S24E, S24L, S24R, A45Q, A45E, A45L, A45R, S101Q, S101E, S101L, S101R, N109Q, N109E, N109L, N109R, K213Q, K213E, K213L, K213R, L217Q, and L217E, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin GG36 that has proteolytic activity and comprises a combination of substitutions selected from S24Q-R45Q-S101Q-G118Q-T213Q, R45Q-S101Q-G118Q-T213Q, S101Q-G118Q-T213Q, G118Q-T213Q, S24E-R45Q-S101Q-G118Q-T213Q, S24E-R45E-S101Q-G118Q-T213Q, S24E-R45E-S101E-G118Q-T213Q, S24E-R45E-S101E-Q109E-G118Q-T213Q, S24E-R45E-S101E-Q109E-G118E-T213Q, S24E-R45E-S101E-Q109E-G118E-T213E, S24L-R45Q-S101Q-G118Q-T213Q, S24L-R45L-S101Q-G118Q-T213Q, S24L-R45L-S101L-G118Q-T213Q, S24L-R45L-S101L-Q109L-G118Q-T213Q, S24L-R45L-S101L-Q109L-G118L-T213Q, S24L-R45L-S101L-Q109L-G118L-T213L, S24R-R45Q-S101Q-G118Q-T213Q, S24R-S101Q-G118Q-T213Q, S24R-S101R-G118Q-T213Q, S24R-S101R-Q109R-G118Q-T213Q, S24R-S101R-Q109R-G118R-T213Q, S24R-S101R-Q109R-G118R-T213R, S24E-S101R-Q109R-G118R-T213R, S24E-R45E-S101R-Q109R-G118R-T213R, S24E-R45E-S101E-Q109R-G118R-T213R, S24E-R45E-S101E-Q109E-G118R-T213R, S24E-R45E-S101E-Q109E-G118E-T213R, S24E-R45E-S101E-Q109E-G118E-T213E, S24Q-R45Q-S101Q-G118Q-T213Q-L217Q, and S24Q-R45Q-S101Q-G118Q-T213Q-L217E, wherein the positions are numbered by correspondence with the amino acid sequence of *B. amyloliquefaciens* subtilisin BPN' set forth as SEQ ID NO:1. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin GG36 that has proteolytic activity and comprises the substitution T213Q, wherein said position is numbered by correspondence with the amino acid sequence of *B. amyloliquefaciens* subtilisin BPN' set forth as SEQ ID NO:1. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the invention provides a cleaning composition that comprises at least one protease variant that is the mature form of an isolated subtilisin variant of a *Bacillus* subtilisin FNA that has proteolytic activity and comprises a combination of substitutions selected from S24Q-A45Q-S101Q-N109Q-N118Q-K213Q, A45Q-S101Q-N109Q-N118Q-K213Q, S101Q-N109Q-N118Q-K213Q, N109Q-N118Q-K213Q, N118Q-K213Q, S24E-A45Q-S101Q-N109Q-N118Q-K213Q, S24E-A45E-S101Q-N109Q-N118Q-K213Q, S24E-A45E-S101E-N109Q-N118Q-K213Q, S24E-A45E-S101E-N109E-N118Q-K213Q, S24E-A45E-S101E-N109E-N118E-K213Q, S24E-A45E-S101E-N109E-N118E-K213E, S24L-A45Q-S101Q-N109Q-N118Q-K213Q, S24L-A45L-S101Q-N109Q-N118Q-K213Q, S24L-A45L-S101L-N109Q-N118Q-K213Q, S24L-A45L-S101L-N109L-N118Q-K213Q, S24L-A45L-S101L-N109L-N118L-K213Q, S24L-A45L-S101L-N109L-N118L-K213L, S24R-A45Q-S101Q-N109Q-N118Q-K213Q, S24R-A45R-S101Q-N109Q-N118Q-K213Q, S24R-A45R-S101R-N109Q-N118Q-K213Q, S24R-A45R-S101R-N109R-N118Q-K213Q, S24R-A45R-S101R-N109R-N118R-K213Q, S24R-A45R-S101R-N109R-N118R-K213R, S24E-A45R-S101R-N109R-N118R-K213R, S24E-A45E-S101R-N109R-N118R-K213R, S24E-A45E-S101E-N109R-N118R-K213R, S24E-A45E-S101E-N109E-N118R-K213R, S24E-A45E-S101E-N109E-N118E-K213R, S24E-A45E-S101E-N109E-N118E-K213E, S24Q-A45Q-S101Q-N109Q-N118Q-K213Q-L217Q, and S24Q-A45Q-S101Q-N109Q-N118Q-K213Q-L217E, wherein the positions correspond to the positions of BPN' subtilisin of SEQ ID NO:1. In some embodiments, the cleaning composition is a detergent. In other embodiments, the detergent is a dish detergent. In yet other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin FNA that has proteolytic activity and comprises the substitution K213Q, wherein said position is numbered by correspondence with the amino acid sequence of *B. amyloliquefaciens* subtilisin BPN' set forth as SEQ ID NO:1. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin that has proteolytic activity and comprises a substitution two or more positions selected from positions 24, 45, 101, 109, 118, 213 and 217, wherein the positions are numbered by correspondence with the amino acid sequence of *B. amyloliquefaciens* subtilisin BPN' set forth as SEQ ID NO:1, and that further comprises one or more additional enzymes or enzyme derivatives. The additional enzymes or enzyme derivatives are selected from hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin that has proteolytic activity and comprises a substitution two or more positions selected from positions 24, 45, 101, 109, 118, 213 and 217, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5, and that further comprises one or more additional enzymes or enzyme derivatives. The additional enzymes or enzyme derivatives are selected from hemicellulases, peroxidases, proteases, metalloproteases, cellulases, xylanases, lipases, phospholipases, esterases, perhydrolases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of *Bacillus* subtilisin GG36 that has proteolytic activity and comprises two or more substitutions at two or more positions selected from S24Q, S24E, S24L, S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions are numbered by correspondence with the amino acid sequence of *B. amyloliquefaciens* subtilisin BPN' set forth as SEQ ID NO:1, and that further comprises one or more additional enzymes or enzyme derivatives. The additional enzymes or enzyme derivatives are selected from hemicellulases, peroxidases, proteases, metalloproteases, cellulases, xylanases, lipases, phospholipases, esterases, perhydrolases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of *Bacillus* subtilisin GG36 that has proteolytic activity and comprises two or more substitutions at two or more positions selected from: S24Q, S24E, S24L, S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5, and that further comprises one or more additional enzymes or enzyme derivatives. The additional enzymes or enzyme derivatives are selected from hemicellulases, peroxidases, proteases, metalloproteases, cellulases, xylanases, lipases, phospholipases, esterases, perhydrolases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of *Bacillus* subtilisin FNA that has proteolytic activity and comprises two or more substitutions at two or more positions selected from S24Q, S24E, S24L, S24R, A45Q, A45E, A45L, A45R, S101Q, S101E, S101L, S101R, N109Q, N109E, N109L, N109R, K213Q, K213E, K213L, K213R, L217Q, and L217E, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5, and that further comprises one or more additional enzymes or enzyme derivatives. The additional enzymes or enzyme derivatives are selected from hemicellulases, peroxidases, proteases, metalloproteases, cellulases, xylanases, lipases, phospholipases, esterases, perhydrolases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin GG36 that has proteolytic activity and comprises a combination of substitutions selected from S24Q-R45Q-S101Q-G118Q-T213Q, R45Q-S101Q-G118Q-T213Q, S101Q-G118Q-T213Q, G118Q-T213Q, S24E-R45Q-S101Q-G118Q-T213Q, S24E-R45E-S101Q-G118Q-T213Q, S24E-R45E-S101E-G118Q-T213Q, S24E-R45E-S101E-Q109E-G118Q-T213Q, S24E-R45E-S101E-Q109E-G118E-T213Q, S24E-R45E-S101E-Q109E-G118E-T213E, S24L-R45Q-S101Q-G118Q-T213Q, S24L-R45L-S101Q-G118Q-T213Q, S24L-R45L-S101L-G118Q-T213Q, S24L-R45L-S101L-Q109L-G118Q-T213Q, S24L-R45L-S101L-Q109L-G118L-T213Q, S24L-R45L-S101L-Q109L-G118L-T213L, S24R-R45Q-S101Q-G118Q-T213Q, S24R-S101Q-G118Q-T213Q, S24R-S101R-G118Q-T213Q, S24R-S101R-Q109R-G118Q-T213Q, S24R-S101R-Q109R-G118R-T213Q, S24R-S101R-Q109R-G118R-T213R, S24E-S101R-Q109R-G118R-T213R, S24E-R45E-S101R-Q109R-G118R-T213R, S24E-R45E-S101E-Q109R-G118R-T213R, S24E-R45E-S101E-Q109E-G118R-T213R, S24E-R45E-S101E-Q109E-G118E-T213R, S24E-R45E-S101E-Q109E-G118E-T213E, S24Q-R45Q-S101Q-G118Q-T213Q-L217Q, and S24Q-R45Q-S101Q-G118Q-T213Q-L217E, wherein the positions are numbered by correspondence with the amino acid sequence of *B. amyloliquefaciens* subtilisin BPN' set forth as SEQ ID NO:1, and that further comprises one or more additional enzymes or enzyme derivatives. The additional enzymes or enzyme derivatives are selected from hemicellulases, peroxidases, proteases, metalloproteases, cellulases, xylanases, lipases, phospholipases, esterases, perhydrolases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin GG36 that has proteolytic activity and comprises the substitution T213Q, wherein said position is numbered by correspondence with the amino acid sequence of *B. amyloliquefaciens* subtilisin BPN' set forth as SEQ ID NO:1, and that further comprises one or more additional enzymes or enzyme derivatives. The additional enzymes or enzyme derivatives are selected from hemicellulases, peroxidases, proteases, metalloproteases, cellulases, xylanases, lipases, phospholipases, esterases, perhydrolases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin FNA that has proteolytic activity and comprises a combination of substitutions selected from S24Q-A45Q-S101Q-N109Q-N118Q-K213Q, A45Q-S101Q-N109Q-N118Q-K213Q, S101Q-N109Q-N118Q-K213Q, N109Q-N118Q-K213Q, N118Q-K213Q, S24E-A45Q-S101Q-N109Q-N118Q-K213Q, S24E-A45E-S101Q-N109Q-N118Q-K213Q, S24E-A45E-S101E-N109Q-N118Q-K213Q, S24E-A45E-S101E-N109E-N118Q-K213Q, S24E-A45E-S101E-N109E-N118E-K213Q, S24E-A45E-S101E-N109E-N118E-K213E, S24L-A45Q-S101Q-N109Q-N118Q-K213Q, S24L-A45L-S101Q-N109Q-N118Q-K213Q, S24L-A45L-S101L-N109Q-N118Q-K213Q, S24L-A45L-S101L-N109L-N118Q-K213Q, S24L-A45L-S101L-N109L-N118L-K213Q, S24L-A45L-S101L-N109L-N118L-K213L, S24R-A45Q-S101Q-N109Q-N118Q-K213Q, S24R-A45R-S101Q-N109Q-N118Q-K213Q, S24R-A45R-S101R-N109Q-N118Q-K213Q, S24R-A45R-S101R-N109R-N118Q-K213Q, S24R-A45R-S101R-N109R-N118R-K213Q, S24R-A45R-S101R-N109R-N118R-K213R, S24E-A45R-S101R-N109R-N118R-K213R, S24E-A45E-S101R-N109R-N118R-K213R, S24E-A45E-S101E-N109R-N118R-K213R, S24E-A45E-S101E-N109E-N118R-K213R, S24E-A45E-S101E-N109E-N118E-K213R, S24E-A45E-S101E-N109E-N118E-K213E, S24Q-A45Q-S101Q-N109Q-N118Q-K213Q-L217Q, and S24Q-A45Q-S101Q-N109Q-N118Q-K213Q-L217E, wherein the positions correspond to the positions of BPN' subtilisin of SEQ ID NO:1, and that further comprises one or more additional enzymes or enzyme derivatives. The additional enzymes or enzyme derivatives are selected from hemicellulases, peroxidases, proteases, metalloproteases, cellulases, xylanases, lipases, phospholipases, esterases, perhydrolases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In other embodiments, the detergent is a dish detergent. In yet other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least one protease variant that is the mature form of an isolated subtilisin variant of a *Bacillus* subtilisin FNA that has proteolytic activity and comprises the substitution K213Q, wherein said position is numbered by correspondence with the amino acid sequence of *B. amyloliquefaciens* subtilisin BPN' set forth as SEQ ID NO:1, and that further comprises one or more additional enzymes or enzyme derivatives. The additional enzymes or enzyme derivatives are selected from hemicellulases, peroxidases, proteases, metalloproteases, cellulases, xylanases, lipases, phospholipases, esterases, perhydrolases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, the cleaning composition is a detergent. In some embodiments, the detergent is a dish detergent. In other embodiments, the detergent is a laundry detergent e.g. heavy duty liquid or dry laundry detergent. In alternative embodiments, the cleaning composition further comprises at least one stabilizing agent.

In another embodiment, the cleaning composition comprises at least 0.0001 weight percent of at least one subtilisin variant that is the mature form of an isolated subtilisin variant of a *Bacillus* subtilisin that has proteolytic activity and comprises a substitution two or more positions selected from positions 24, 45, 101, 109, 118, 213 and 217, wherein the positions are numbered by correspondence with the amino acid sequence of *B. amyloliquefaciens* subtilisin BPN' set forth as SEQ ID NO:1.

In another embodiment, the cleaning composition comprises at least 0.0001 weight percent of at least one subtilisin variant that is the mature form of an isolated subtilisin variant of a *Bacillus* subtilisin that has proteolytic activity and comprises a substitution two or more positions selected from positions 24, 45, 101, 109, 118, 213 and 217, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5.

In another embodiment, the cleaning composition comprises at least 0.0001 weight percent of at least one subtilisin variant that is the mature form of an isolated subtilisin variant of *Bacillus* subtilisin GG36 that has proteolytic activity and comprises two or more substitutions at two or more positions selected from S24Q, S24E, S24L, S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions are numbered by correspondence with the amino acid sequence of *B. amyloliquefaciens* subtilisin BPN' set forth as SEQ ID NO:1.

In another embodiment, the cleaning composition comprises at least 0.0001 weight percent of at least one subtilisin variant that is the mature form of an isolated subtilisin variant of *Bacillus* subtilisin GG36 that has proteolytic activity and comprises two or more substitutions at two or more positions selected from : S24Q, S24E, S24L,S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5.

In another embodiment, the invention provides a cleaning composition comprising at least 0.0001 weight percent of at least one subtilisin variant that is the mature form of an isolated subtilisin variant of *Bacillus* subtilisin FNA that has proteolytic activity and comprises two or more substitutions at two or more positions selected from S24Q, S24E, S24L, S24R, A45Q, A45E, A45L, A45R, S101Q, S101E, S101L, S101R, N109Q, N109E, N109L, N109R, K213Q, K213E, K213L, K213R, L217Q, and L217E, wherein the positions are numbered by correspondence with the amino acid sequence of *B. amyloliquefaciens* subtilisin BPN' set forth as SEQ ID NO:1.

In another embodiment, the cleaning composition comprises at least 0.0001 weight percent of at least one subtilisin variant that is the mature form of an isolated subtilisin variant of *Bacillus* subtilisin FNA that has proteolytic activity and comprises two or more substitutions at two or more positions selected from S24Q, S24E, S24L, S24R, A45Q, A45E, A45L, A45R, S101Q, S101E, S101L, S101R, N109Q, N109E, N109L, N109R, K213Q, K213E, K213L, K213R, L217Q, and L217E, wherein the positions are numbered by correspondence with the amino acid sequence of *B. amyloliquefaciens* subtilisin BPN' set forth as SEQ ID NO:1, and that has a relative protein expression level performance index (TCA PI) and/or a stain removal activity performance index (BMI PI) that is greater or equal to 0.5.

In another embodiment, the cleaning composition comprises at least 0.0001 weight percent of at least one subtilisin variant that is the mature form of an isolated subtilisin variant of a *Bacillus* subtilisin GG36 that has proteolytic activity and comprises a combination of substitutions selected from S24Q-R45Q-S101Q-G118Q-T213Q, R45Q-S101Q-G118Q-T213Q, S101Q-G118Q-T213Q, G118Q-T213Q, S24E-R45Q-S101Q-G118Q-T213Q, S24E-R45E-S101Q-G118Q-T213Q, S24E-R45E-S101E-G118Q-T213Q, S24E-R45E-S101E-Q109E-G118Q-T213Q, S24E-R45E-S101E-Q109E-G118E-T213Q, S24E-R45E-S101E-Q109E-G118E-T213E, S24L-R45Q-S101Q-G118Q-T213Q, S24L-R45L-S101Q-G118Q-T213Q, S24L-R45L-S101L-G118Q-T213Q, S24L-R45L-S101L-Q109L-G118Q-T213Q, S24L-R45L-S101L-Q109L-G118L-T213Q, S24L-R45L-S101L-Q109L-G118L-T213L, S24R-R45Q-S101Q-G118Q-T213Q, S24R-S101Q-G118Q-T213Q, S24R-S101R-G118Q-T213Q, S24R-S101R-Q109R-G118Q-T213Q, S24R-S101R-Q109R-G118R-T213Q, S24R-S101R-Q109R-G118R-T213R, S24E-S101R-Q109R-G118R-T213R, S24E-R45E-S101R-Q109R-G118R-T213R, S24E-R45E-S101E-Q109R-G118R-T213R, S24E-R45E-S101E-Q109E-G118R-T213R, S24E-R45E-S101E-Q109E-G118E-T213R, S24E-R45E-S101E-Q109E-G118E-T213E, S24Q-R45Q-S101Q-G118Q-T213Q-L217Q, and S24Q-R45Q-S101Q-G118Q-T213Q-L217E, wherein the positions are numbered by correspondence with the amino acid sequence of *B. amyloliquefaciens* subtilisin BPN' set forth as SEQ ID NO:1.

In another embodiment, the cleaning composition comprises at least 0.0001 weight percent of at least one subtilisin variant that is the mature form of an isolated subtilisin variant of a *Bacillus* subtilisin GG36 that has proteolytic activity and comprises the substitution T213Q, wherein said position is numbered by correspondence with the amino acid sequence of *B. amyloliquefaciens* subtilisin BPN' set forth as SEQ ID NO:1.

In another embodiment, the cleaning composition comprises at least 0.0001 weight percent of at least one subtilisin variant that is the mature form of an isolated subtilisin variant of a *Bacillus* subtilisin FNA that has proteolytic activity and comprises a combination of substitutions selected from S24Q-A45Q-S101Q-N109Q-N118Q-K213Q, A45Q-S101Q-N109Q-N118Q-K213Q, S101Q-N109Q-N118Q-K213Q, N109Q-N118Q-K213Q, N118Q-K213Q, S24E-A45Q-S101Q-N109Q-N118Q-K213Q, S24E-A45E-S101Q-N109Q-N118Q-K213Q, S24E-A45E-S101E-N109Q-N118Q-K213Q, S24E-A45E-S101E-N109E-N118Q-K213Q, S24E-A45E-S101E-N109E-N118E-K213Q, S24E-A45E-S101E-N109E-N118E-K213E, S24L-A45Q-S101Q-N109Q-N118Q-K213Q, S24L-A45L-S101Q-N109Q-N118Q-K213Q, S24L-A45L-S101L-N109Q-N118Q-K213Q, S24L-A45L-S101L-N109L-N118Q-K213Q, S24L-A45L-S101L-N109L-N118L-K213Q, S24L-A45L-S101L-N109L-N118L-K213L, S24R-A45Q-S101Q-N109Q-N118Q-K213Q, S24R-A45R-S101Q-N109Q-N118Q-K213Q, S24R-A45R-S101R-N109Q-N118Q-K213Q, S24R-A45R-S101R-N109R-N118Q-K213Q, S24R-A45R-S101R-N109R-N118R-K213Q, S24R-A45R-S101R-N109R-N118R-K213R, S24E-A45R-S101R-N109R-N118R-K213R, S24E-A45E-S101R-N109R-N118R-K213R, S24E-A45E-S101E-N109R-N118R-K213R, S24E-A45E-S101E-N109E-N118R-K213R, S24E-A45E-S101E-N109E-N118E-K213R, S24E-A45E-S101E-N109E-N118E-K213E, S24Q-A45Q-S101Q-N109Q-N118Q-K213Q-L217Q, and S24Q-A45Q-S101Q-N109Q-N118Q-K213Q-L217E, wherein the positions correspond to the positions of BPN' subtilisin of SEQ ID NO:1.

In another embodiment, the cleaning composition comprises at least 0.0001 weight percent of at least one subtilisin variant that is the mature form of an isolated subtilisin variant of a *Bacillus* subtilisin FNA that has proteolytic activity and comprises the substitution K213Q, wherein said position is numbered by correspondence with the amino acid sequence of *B. amyloliquefaciens* subtilisin BPN' set forth as SEQ ID NO:1.

In another embodiment, the invention provides a method of cleaning that comprises contacting a surface and/or an article comprising a fabric with any one of the cleaning compositions described, and optionally washing and/or rinsing said surface or article.

BRIEF DESCRIPTION OF THE DRAWINGS

FIG. 1 provides an alignment of the mature form of parent proteases GG36 (SEQ ID:4) and FNA (SEQ ID NO:7) with BPN' (SEQ ID NO:1). Unless otherwise specified, substitution positions are given in relationship to BPN'

FIG. 2 provides a charge change matrix indicating the charge change for amino acid residue substitutions at pH 8.6. From this matrix the net charge change of a variant enzyme as compared to a parent enzyme can be easily determined.

FIG. 3 provides a Kyte-Doolittle hydropathicity change matrix indicating the hydropathicity change for amino acid residue substitutions. From this matrix the net hydropathicity change of a variant enzyme as compared to a parent enzyme can be easily determined.

DETAILED DESCRIPTION OF THE INVENTION

Figure 4:
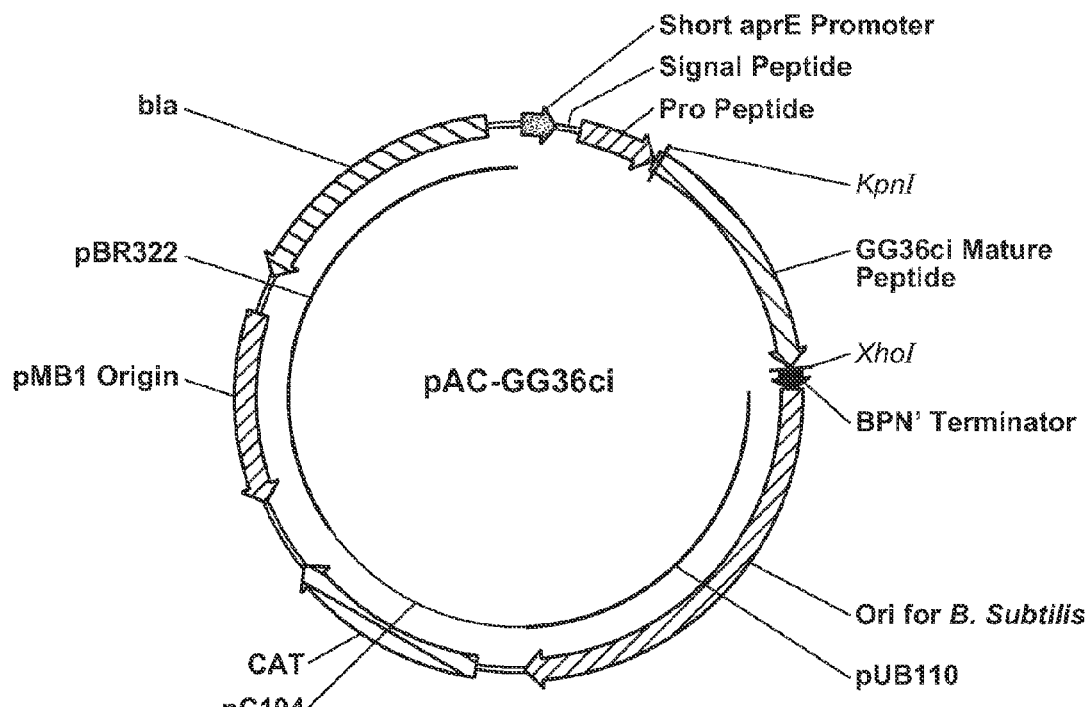
FIG. 4 provides a map of pAC-GG36ci

The present invention provides engineered protease variants. In particular, the protease variants comprise combinable mutations at selected surface positions that affect the charge and/or hydrophobicity of the enzyme to enhance at least one desired property of the resulting variant enzyme in a chosen application. Compositions comprising the protease variants, and methods for using the same are also provided.

As indicated herein, introducing substitutions that affect the charge and/or hydrophobicity of subtilisin results in an enzyme that comprises at least one combinable mutation to provide a variant protease having a Performance Index for at least one property of interest being a performance index >0.5 when compared to that of the parent enzyme. The combinable mutations serve to enhance the performance index for at least one desired enzyme property in a variety of applications. Properties of interest include but are not limited to charge, hydrophobicity, solubility, cleaning performance e.g. stain removal from fabric and/or hard surfaces, thermal stability, storage stability, detergent stability, substrate binding, enzyme inhibition, expression level, reaction rate, and substrate degradation. In some embodiments, the property of interest is one or more properties selected from charge, hydrophobicity, expression level (TCA PI) and cleaning performance e.g. stain removal (BMI PI). Although described herein in relationship to proteases and blood, milk and ink stains (BMI), it is contemplated that the protease variants of the present invention are optimized for any enzyme-substrate interaction in any a variety of reaction media dictated by the application e.g. cleaning applications.

Previously, efforts to develop superior proteins focused upon minimizing enzyme binding to surfaces. For example, some methods involved altering the subtilisin sequence to obtain variant enzymes with decreased adsorption to insoluble substrates (See e.g., WO 95/07991). In another approach, the pI of subtilisin was altered in order to obtain variant enzymes with a net charge of zero at a defined pH (See e.g., WO 91/00345). However, as determined during development of the present invention, these approaches are not always successful. During the development of the present invention, it was determined that surface properties of enzymes generally have optima that are determined as a function of change in surface charge and/or hydrophobicity. Even for enzymes that are normally quite active, surface properties can cause the overall reaction to be much slower under some conditions and with some substrates than under other conditions and/or with other substrates. In some embodiments the present invention provides variant proteases that comprise modified surface properties obtained by changing the nature of one or more amino acids on the enzyme surface. When these changes are made at sites on the surface that do not interact with any other amino acids and are not necessary for enzyme function, the properties of the protein are predicted based on the properties of the amino acids substituted at those positions as described herein.

Sites are readily identified from structure data; alternatively, homologous sequence alignments, site evaluation library data and/or any combination thereof find use. Amino acid scoring matrices (e.g. FIG. 1) and/or hydrophobicity scales (e.g. FIG. 2) find use in guiding amino acid substitution(s) and to identify those physical properties of the protein that correlate with the properties of the substituted amino acids.

Definitions

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works well known to those skilled in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, some of the preferred methods and materials are described herein. Accordingly, the terms defined immediately below are more fully described by reference to the Specification as a whole.

Also, as used herein, the singular "a," "an," and "the" include the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, a number of terms are defined below.

As used herein, there term "performance index (PI)" refers to the ratio of the performance of a variant enzyme relative to that of the parent or reference enzyme in a given assay. The PI for cleaning performance is provided herein as the performance to remove blood, milk, and ink stains (BMI), and is provided as a BMI PI value. The PI for expression level performance is provided herein as the level of protein produced as measured by trichloroacteic (TCA) acid precipitation, and is provided as a TCA PI value.

As used herein, "combinable mutations" are those mutations for which the variant comprising the mutations has Performance Index (PI) a value >0.5 for at least one property. Combinable mutations are mutations that can be combined to deliver proteins with appropriate Performance Indices for one or more desired properties, and have changes in charge and/or hydrophobicity. Positions at which mutations occur are classed as follows: Non-restrictive positions have =20% neutral mutations for at least one property; and Restrictive positions have <20% neutral mutations for activity and stability.

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78 [1985]). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. An isolated protein is more than about 10% pure, preferably more than about 20% pure, and even more preferably more than about 30% pure, as determined by SDS-PAGE. Further aspects of the invention encompass the protein in a highly purified form (i.e., more than about 40% pure, more than about 60% pure, more than about 70% pure, more than about 80% pure, more than about 90% pure, more than about 95% pure, more than about 97% pure, and even more than about 99% pure), as determined by SDS-PAGE.

As used herein, a "parent" protein refers to the protein that is modified e.g. by introducing one or more amino acid substitutions, to generate one or more variant of the parent protein. Thus, the terms "protease variant" and "variant protease" are used in reference to parent proteases that are similar to variant protease, particularly in their function, but have mutations in their amino acid sequence that make them different in sequence from the parent protease at from one to 20 amino acid positions. The amino acid sequences of the mature region of exemplary parent proteases are shown in the alignment of FIG. 1. FNA (SEQ ID NO:7) and GG36 (SEQ ID NO:4) are the mature parent proteases which have been modified to contain one or more combinable substitutions to generate the variant proteases of the invention. GG36 is a wild-type *Bacillus lentus* protease, and FNA is the *Bacillus amyloliquefaciens* BPN'portease containing the Y217L substitution.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), Advances in Biochemical Engineering/Biotechnology, [1988]). For example, proteolytic activity may be ascertained by comparative assays which analyze the respective protease's ability to hydrolyze a commercial substrate. Exemplary substrates useful in the analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference). The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the term "subtilisin" refers any member of the S8 serine protease family as described in MEROPS—The Peptidase Data base (Rawlings et al., MEROPS: the peptidase database, Nucleic Acids Res, 34 Database issue, D270-272, 2006, at the website merops.sanger.ac.uk/cgi-bin/merops.cgi?id=s08;action=.). The following information was derived from MEROPS—The Peptidase Data base as of Nov. 6, 2008 "Peptidase family S8 contains the serine endopeptidase subtilisin and its homologues (Biochem J, 290:205-218, 1993) Family S8, also known as the subtilase family, is the second largest family of serine peptidases, and can be divided into two subfamilies, with subtilisin (S08.001) the type-example for subfamily S8A and kexin (S08.070) the type-example for subfamily S8B. Tripeptidyl-peptidase II (TPP-II; S08.090) was formerly considered to be the type-example of a third subfamily, but has since been determined to be misclassified. Members of family S8 have a catalytic triad in the order Asp, His and Ser in the sequence, which is a different order to that of families S1, S9 and S10. In subfamily S8A, the active site residues frequently occurs in the motifs Asp-Thr/Ser-Gly (which is similar to the sequence motif in families of aspartic endopeptidases in clan AA), His-Gly-Thr-His (SEQ ID NO: 8) and Gly-Thr-Ser-Met-Ala-Xaa-Pro (SEQ ID NO: 9). In subfamily S8B, the catalytic residues frequently occur in the motifs Asp-Asp-Gly, His-Gly-Thr-Arg (SEQ ID NO: 10) and Gly-Thr-Ser-Ala/Val-Ala/Ser-Pro (SEQ ID NO: 11). Most members of the S8 family are endopeptidases, and are active at neutral-mildly alkali pH. Many peptidases in the family are thermostable. Casein is often used as a protein substrate and a typical synthetic substrate is suc-AAPF. Most members of the family are nonspecific peptidases with a preference to cleave after hydrophobic residues. However, members of subfamily S8B, such as kexin (S08.070) and furin (S08.071), cleave after dibasic amino acids. Most members of the S8 family are inhibited by general serine peptidase inhibitors such as DFP and PMSF. Because many members of the family bind calcium for stability, inhibition can be seen with EDTA and EGTA, which are often thought to be specific inhibitors of metallopeptidases. Protein inhibitors include turkey ovomucoid third domain (I01.003), *Streptomyces* subtilisin inhibitor (I16.003), and members of family I13 such as eglin C (I13.001) and barley inhibitor CI-1A (I13.005), many of which also inhibit chymotrypsin (S01.001). The subtilisin propeptide is itself inhibitory, and the homologous proteinase B inhibitor from *Saccharomyces* inhibits cerevisin (S08.052). The tertiary structures for several members of family S8 have now been determined. A typical S8 protein structure consists of three layers with a seven-stranded β sheet sandwiched between two layers of helices. Subtilisin (S08.001) is the type structure for clan SB (SB). Despite the different structure, the active sites of subtilisin and chymotrypsin (S01.001) can be superimposed, which suggests the similarity is the result of convergent rather than divergent evolution.

As used herein, the terms "*Bacillus*" and "genus *Bacillus*" include all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*GeoBacillus stearothermophilus.*" The production of resistant endospores in the presence of oxygen is considered the defining feature of the genus *Bacillus*, although this characteristic also applies to the recently named *AlicycloBacillus, AmphiBacillus, AneuriniBacillus, AnoxyBacillus, BreviBacillus, FiloBacillus, GraciliBacillus, HaloBacillus, PaeniBacillus, SaliBacillus, ThermoBacillus, UreiBacillus*, and *VirgiBacillus*.

The terms "protein" and "polypeptide" are used interchangeability herein. The 3-letter code for amino acids as defined in conformity with the IUPAC-IUB Joint Commission on Biochemical Nomenclature (JCBN) is used throughout this disclosure. It is also understood that a polypeptide may be coded for by more than one nucleotide sequence due to the degeneracy of the genetic code.

A "prosequence" is an amino acid sequence between the signal peptide and the mature region of a protease. The prosequence is cleaved during the maturation process that results in the production of the active mature form of the protease.

The term "signal sequence" or "signal peptide" refers to any sequence of nucleotides and/or amino acids that participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *B. subtilis* subtilisin fused to the remainder of the signal sequence of the subtilisin from *B. lentus* (ATCC 21536).

The term "hybrid signal sequence" refers to signal sequences in which part of sequence is obtained from the expression host fused to the signal sequence of the gene to be expressed. In some embodiments, synthetic sequences are utilized.

The term "mature" form of a protein or peptide refers to the final functional form of the protein or peptide. To exemplify, the mature form of the FNA protease provided herein includes the amino acid sequence of SEQ ID NO:7, while a mature form of the GG36 protease includes the amino acid sequence of SEQ ID NO:4.

The term "precursor" herein refers to the form of a protein or peptide having a prosequence operably linked to the amino or carbonyl terminus of the mature protein. To exemplify, SEQ ID NOS:3 and 6 are sequences of the precursors of the mature GG36 (SEQ ID NO:4) and FNA (SEQ ID NO:7), respectively. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" and "naturally occurring protein" refer to an enzyme or protein having the unmodified amino acid sequence identical to that found in nature. Naturally occurring enzymes include native enzymes, those enzymes naturally expressed or found in the particular microorganism.

The terms "derived from" and "obtained from" refer to not only an enzyme (e.g., protease) produced or producible by a strain of the organism in question, but also an enzyme encoded by a DNA sequence isolated from such strain and produced in a host organism containing such DNA sequence. Additionally, the term refers to a enzyme that is encoded by a DNA sequence of synthetic and/or cDNA origin and which has the identifying characteristics of the enzyme in question.

A "derivative" within the scope of this definition generally retains the characteristic proteolytic activity observed in the wild-type, native or parent form to the extent that the derivative is useful for similar purposes as the wild-type, native or parent form. Functional enzyme derivatives encompass naturally occurring, synthetically or recombinantly produced peptides or peptide fragments having the general characteristics of the parent enzyme.

As used herein, "by correspondence to" refers to a residue at the enumerated position in a protein or peptide.

As used herein, "substituted" and "substitutions" refer to replacement(s) of one or more amino acid residues or nucleic acid bases in a parent sequence. In some embodiments, the substitution involves the replacement of a naturally occurring residue or base. In some embodiments, two or more amino acids are substituted to generate a variant protease that comprises a combination of amino acid substitutions. In some embodiments, combinations of substitutions are denoted by the amino acid position at which the substitution is made. For example, a combination denoted by E6A-E30G means that glutamic acid (E) at position 6 is substituted with Alanine (A) and the glutamic acid (E) at position 30 is substituted with a Glycine (G) Amino acid positions are given by correspondence to the numbered position in the mature region of the subtilisin BPN' (SEQ ID NO:1).

The phrase "substitution at two or more positions" herein refers to a combination of two or more substitutions that are made in the same protein. Thus, "a substitution at two or more positions" refers to any one of a combination of 2, 3, 4, 5, 6, and 7 amino acid substitutions.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the protease (e.g., precursor or mature protease) that is operably linked to a suitable prosequence (e.g., secretory, etc.) capable of effecting the expression of the DNA in a suitable host.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein, the terms "Host strain" or "host cell" refers to a suitable host for an expression vector comprising DNA according to the present invention.

As used herein, "cleaning compositions" and "cleaning formulations" refer to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, powder or spray composition), used in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, dry e.g. granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., fabric) surface cleaning compositions, including but not limited to dishwashing detergent compositions, oral cleaning compositions, denture cleaning compositions, and personal cleansing compositions.

As used herein, the terms "detergent composition" and "detergent formulation" are used in reference to mixtures which are intended for use in a wash medium for the cleaning of soiled objects. In preferred embodiments, the term is used in reference to detergents used to clean dishes, cutlery, etc. (e.g., "dish detergents" or "dishwashing detergents"). It is not intended that the present invention be limited to any particular detergent formulation or composition. Indeed, it is intended that in addition to detergents that contain at least one protease of the present invention, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, "dishwashing composition" refers to all forms of compositions for cleaning dishware, including cutlery, including but not limited to granular and liquid forms. It is not intended that the present invention be limited to any particular type or dishware composition. Indeed, the present invention finds use in cleaning dishware (e.g., dishes, including, but not limited to plates, cups, glasses, bowls, etc.) and cutlery (e.g., utensils, including but not limited to spoons, knives, forks, serving utensils, etc.) of any material, including but not limited to ceramics, plastics, metals, china, glass, acrylics, etc. The term "dishware" is used herein in reference to both dishes and cutlery.

As used herein, "non-phosphate containing dishwashing detergents" are detergents that contain no more than 0.5% phosphorus (i.e., phosphorus is a trace element).

As used herein, "wash performance" or "cleaning performance" of a variant protease refers to the contribution made by a variant protease to the cleaning ability of a cleaning composition when compared to that obtained in the absence of the protease variant.

The term "relevant washing conditions" is used herein to indicate the conditions, particularly washing temperature, time, washing mechanics, sud concentration, type of detergent and water hardness, actually used in households in a dish or laundry detergent market segment.

The term "improved wash performance" is used to indicate that a better end result is obtained in stain removal under relevant washing conditions, or that less variant protease, on weight basis, is needed to obtain the same end result relative to the corresponding wild-type or starting parent protease.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

As used herein, "effective amount of enzyme" refers to the quantity of enzyme necessary to achieve the enzymatic activity required in the specific application (e.g., personal care product, cleaning composition, etc.). Such effective amounts are readily ascertained by one of ordinary skill in the art and are based on many factors, such as the particular enzyme variant used, the cleaning application, the specific composition of the cleaning composition, and whether a liquid or dry (e.g., granular, bar) composition is required, and the like.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. A preferred filler salt is sodium sulfate.

As used herein, "adjunct ingredient" or "adjunct material" refers to cleaning materials that include, but are not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference).

As used herein, "dishwashing composition" refers to all forms for compositions for cleaning dishes, including but not limited to granular and liquid forms.

As used herein, "fabric cleaning composition" refers to all forms of detergent compositions for cleaning fabrics, including but not limited to, granular, liquid and bar forms.

As used herein, "fabric" encompasses any textile material. Thus, it is intended that the term encompass garments, as well as fabrics, yarns, fibers, non-woven materials, natural materials, synthetic materials, and any other textile material.

As used herein, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, "textile materials" is a general term for fibers, yarn intermediates, yarn, fabrics, and products made from fabrics (e.g., garments and other articles).

Most strategies currently utilized for improving protein performance in industrial, consumer or pharmaceutical applications have focused on amino acid substitutions at or near an enzyme's active site, in order to increase catalytic efficiency. However, during the development of the present invention, it was determined that mutations elsewhere on the enzyme surface dramatically increase enzyme performance beyond what is possible through catalytic efficiency improvements. Basically, the reaction rate governing conversion of substrates to products mediated by enzymes is only partially controlled by the rate of the chemical catalytic conversion step alone. Enzymes and substrates interact as colloids prior to their association as an enzyme-substrate ES complex, as well as during dissociation from the enzyme-product EP complex that is formed after chemical conversion. Even if the reaction step proceeds at a fast rate, enzyme approach towards substrate can be extremely slow (e.g., diffusion-limited), as in the case of same-sign colloids experiencing electrostatic repulsive forces. Likewise, release of enzyme from the enzyme-product EP complex can be extremely slow (e.g., diffusion-limited), as in the case of colloids experiencing attractive short-range hydrophobic and dispersive forces. Both conditions increase the enzyme transit time from substrate to product and become rate-step limiting compared to chemical conversion. While it is possible to envisage that oppositely-charged colloids would actually accelerate the formation of ES complexes (e.g., above the diffusion limit), subsequent dissociation of the EP complex would be painfully slow (assuming that no charges are created nor lost) and the overall reaction rate would decrease. Therefore, the asymmetry of the pair-wise interaction potential is exploited in order to ensure minimal transit times for both the ES and EP complexes. This is particularly important in industrial biotechnology, since it is desirable to convert all of the substrate to product in the shortest amount of time possible under often enzyme-limited conditions. Historically, protein engineers have focused on specific enzyme-substrate interactions of the chemical conversion step and have failed to recognize the contribution of both short-and long-range non-specific interactions, arising from intermolecular colloidal and surface forces, which govern the association and dissociation steps. An objective of the present invention is to provide protease variants having altered surface properties obtained by changing the nature of one or more amino acids on the enzyme surface that optimize intermolecular forces to the point where the chemical conversion step becomes rate-limiting.

Modification of surface properties is achieved by introducing amino acid substitutions that alter the charge and/or the hydrophobicity of the enzyme using the methods described herein. Once the chemical conversion step becomes rate limiting, further improvements in the performance of the variant enzyme can be achieved through changes in the enzyme active site. This objective is applicable whether the substrate is a small peptide in solution or an insoluble macroscopic substrate. Nonetheless, knowledge of the mechanism(s) involved is not necessary in order to make and use the present invention. Nor is it intended that the present invention be limited to any particular mechanism.

Briefly the methods used to generate the protease variants of the present invention involve (I) Assaying Probe Proteins Spanning a Physical Property Range; (II) Determining Physical Property Optimum for a Given Favorable Outcome; and (III) Providing Variant Proteins Having The Physical Property Optimum.

I. Assay Probe Proteins

Assaying probe proteins involves the testing of multiple probe proteins (i.e., "probe protein folds") spanning the range of a physical property of interest (i.e., a "property of interest") in an appropriate assay. Probe proteins include a limited set of proteins and/or variants thereof. In some exemplary embodiments, at least one serine protease was tested for one or more benefits. For instance, the change in net charge of the variant relative to the parent enzyme for two serine proteases, GG36 and FNA were provided. The net charge change for the variants of GG36 and FNA as described herein, span a relative net charge change range of −7 to 0 as compared to the respective parent enzymes.

II. Determine Physical Property Optimum

Determining the physical property optimum i.e. determining the optimum of a property of interest, involves identifying a physical property optimum or range thereof for a favorable outcome. In some exemplary embodiments, the cleaning performance index, herein provided as the BMI PI of FNA and GG36 protease variants was measured. In other embodiments, the expression level herein provided as the TCA PI of the FNA and GG36 protease variants was measured. In the present embodiments, when comparing benefits obtained with proteins having the same fold i.e. serine proteases, a relative was be employed (e.g., net charge differential relative to wild-type or parent protein). Alternatively, when comparing benefits obtained with proteins having different folds, e.g. serine proteases and metalloproteases, a common physical property scale is employed (e.g., protein charge reported as zeta potential). Probe proteins spanning a wide physical property range are employed, in order to increase the likelihood of defining an optimum for that physical property. Once the optimum value or optimum range for a benefit of interest has been established by assaying the probe proteins, it is possible to predict both the general direction and magnitude of change likely to be required for converting an inferior performer (e.g., lying outside of the optimal range) to a superior performer (e.g., within the optimal range).

Use of more than one probe protein series is contemplated to permit the identification of different physical property optima for a benefit of interest. For instance in some embodiments, both changes in net charge and hydrophobicity relative to that of the parent enzyme of the detergent proteases GG36 and FNA are tested for cleaning performance in a blood, milk, ink assay. In some instances, the same physical property is contemplated to exhibit different optima for different benefits. For example, there exists an optimal protease charge for cleaning performance for FNA (BMI PI), which is distinct from the optimal protease charge for expression level (TCA PI).

In some embodiments, charge-related physical properties are compared across parent and variant proteins in terms of measured zeta potential, net charge, charge density, and/or surface count of ionizable groups. In general, any method of determining protein charge from titration or electrophoretic measurements is suitable for comparing different protein folds. Comparing different protein variants is done by calculation of one or more of the above quantities based upon protein primary, secondary and/or tertiary sequence information when available. Typical bioinformatics tools employed for such purposes include isoelectric point calculators using the Henderson-Hesselbach equation (e.g., European Molecular Biology Laboratory) or Poisson-Boltzmann electrostatic solvers (e.g., DelPhi, MOE).

III. Provide Variant Proteins Having the Physical Property Optimum

Once an optimum value or range has been determined in the previous step, a plurality of candidate proteins are provided which are constrained for the physical property of interest. Suitable methods for providing candidate proteins include, but are not limited to the production of artificial enzymes variants by recombinant techniques, as well as the purification of natural enzyme variants (e.g., homologues) by chromatography, the in vitro synthesis of glycosylation or phosphorylation enzyme variants or the in vitro production of enzyme conjugates. Another way to alter the hydrophobicity of a protein via glycosylation is to generate new glycosylation sites on the surface of the enzyme. These variants will be glycosylated in vivo during expression.

In some embodiments, hydrophobicity-related physical properties are compared across protease variants in terms of the overall contribution by the substituted residues to the net change in hydrophobicity of the resulting variant relative to that of the parent enzyme. In some embodiments, the overall hydrophobic contribution is calculated using one or more of the many amino-acid hydrophobicity scales available in the literature and known to those in the art, that take into account protein primary, secondary and/or tertiary structure information. In instances when hydrophobicity-related physical properties are compared across different protein folds in terms of measured protein partitioning between its native aqueous environment and a hydrophobic phase. Examples include but are not limited to surface tension at the air-water or heptane-water interfaces, as well as contact angle and wetting measurements between aqueous and solid substrate-containing phases. In general, any method suitable for characterizing the partitioning of a protein between two phases is suitable for use in the present invention, including optical (e.g., ellipsometry, surface plasmon resonance, interferometry, and/or reflectivity), acoustic (e.g., quartz-crystal microbalance), fluorescence, spectroscopy (e.g., attenuated total reflection infrared) or concentration (e.g., enzyme activity) determinations.

Charge and hydrophobicity scales are not independent from each other since charged residues add hydrophilic character. Thus, rather than simply choosing one scale over another, some embodiments of the present invention employ multiple different scales (e.g., theoretical or experimentally determined) for identifying physical property dependencies. References for 23 of the most commonly used hydrophobicity scales include: hydrophobicity (Rao and Argos) calculates membrane buried helix parameter. (Rao and Argos, Biochim Biophys. Acta 869:197-214 [1986]); hydrophobicity (Black and Mould) calculates hydrophobicity of physiological L-alpha amino acids (Black and Mould, Anal. Biochem., 193:72-82 [1991]); hydrophobicity (Bull and Breese) calculates hydrophobicity (free energy of transfer to surface in kcal/mole)(Bull and Breese, Arch. Biochem. Biophys. 161:665-670 [1974]); hydrophobicity (Chothia) calculates proportion of residues 95% buried (in 12 proteins) (Chothia, J. Mol. Biol., 105:1-14 [1976]); hydrophobicity (Kyte and Doolittle) calculates hydropathicity (Kyte and Doolittle, J. Mol. Biol., 157:105-132 [1982]); hydrophobicity (Eisenberg et al.) calculates normalized consensus hydrophobicity scale (Eisenberg et al., J. Mol. Biol. 179:125-142 [1984]); hydrophobicity (Fauchere and Pliska) calculates hydrophobicity scale (pi-r) (Fauchere and Pliska, Eur. J. Med. Chem., 18:369-375 [1983]); hydrophobicity (Guy) calculates hydrophobicity scale based on free energy of transfer (kcal/mole) (Guy, Biophys J., 47:61-70 [1985]); hydrophobicity (Janin) calculates free energy of transfer from inside to outside of a globular protein (Janin, Nature 277:491-492 [1979]); hydrophobicity (Abraham and Leo) calculates hydrophobicity (delta G1/2cal) (Abraham and Leo, Proteins: Structure, Function and Genetics 2:130-152 [1987]); hydrophobicity (Manavalan et al.) calculates average surrounding hydrophobicity (Manavalan et al., Nature 275:673-674 [1978]); Hydrophobicity (Miyazawa et al.) calculates hydrophobicity scale (contact energy derived from 3D data) (Miyazawa et al., Macromolecules 18:534-552 [1985]); hydrophobicity (Aboderin) calculates mobilities of amino acids on chromatography paper (RF) (Aboderin, Int. J. Biochem., 2:537-544 [1971]); hydrophobicity HPLC (Parker et al.) calculates hydrophilicity scale derived from HPLC peptide retention times (Parker et al., Biochem., 25:5425-5431 [1986]); Hphob. HPLC pH3.4 calculates hydrophobicity indices at ph 3.4 determined by HPLC (Cowan and Whittaker, Peptide Res., 3:75-80 [1990]); Hphob. HPLC pH7.5 calculates hydrophobicity indices at ph 7.5 determined by HPLC (Cowan and Whittaker, Peptide Res., 3:75-80 [1990]); hydrophobicity (Rose et al.)(AA) calculates the mean fractional area loss (f) [average area buried/standard state area] (Rose et al., Science 229:834-838 [1985]); and hydrophobicity (Roseman) calculates hydrophobicity scale (pi-r) (Roseman, J. Mol. Biol., 200:513-522 [1988]).

Other physical properties that are compared across proteases and variants thereof within the same protein fold or across different protein folds include but are not limited to solubility-related physical properties, size-related physical properties, and protein melting temperatures. Solubility-related physical properties are compared across different protein folds in terms of both charge and hydrophobicity scales previously described. In general, any thermodynamic or kinetic quantity characterizing protein-protein versus protein-solvent interactions is suitable for use with the methods of the present invention. For instance second virial coefficient (See, Wilson, Acta Crystallographica, D50:361-365 [1994]), chi parameter, osmotic pressure, and activity or fugacity coefficients reflecting deviations from ideal mixing behavior find use (See e.g., Reid et al., "The Properties of Gases and Liquids", 4$^{th}$ Ed. McGraw-Hill, [1987]). Size-related physical properties are compared across different protein folds using any experimental means suitable for determining protein or polymer dimensions. Size is inferred from molecular weight using commonly available correlations between protein or polymer conformation (coil, globular, branched), their molecular weight and hydrodynamic or gyration radius. Suitable techniques for size or molecular weight determination include, but are not limited to static and dynamic light scattering, gel electrophoresis, mass spectroscopy and chromatography. Alternatively, size is readily estimated from knowledge of the experimentally determined protein crystal structures or structural homology models.

Protein melting temperatures ($T_m$) are typically determined through monitoring of a physical reporter property across a temperature scan. Suitable methods include, but are not limited to differential scanning calorimetry, circular dichroism, dynamic light scattering, and UV-visible spectroscopy.

Applications for Serine Protease Enzymes

The combinable mutations created to generate the protease variants are contemplated to serve to enhance the performance index e.g. locate the performance optimum, for at least one desired enzyme property in a variety of applications. The location of the performance/property optimum is largely influenced by medium utilized (e.g., detergent formulation, pH, ionic strength, etc), as well as the net charge and charge distribution of amino acid residues of the enzyme of interest. Thus, an optimal enzyme is contemplated to exist for different formulations of varying pH, ionic strength, surfactant type and ratio, builders and chelators, all of which affect electrostatic phenomena. The use of enzyme blends, in which each member of the blend possesses a different charge optimum, is contemplated for the production of formulations suitable for a wide range of conditions (e.g., proteases in detergent formulations sold in different geographies or locales having differences in water hardness). The use of enzyme blends, in which each member of the blend excels in the cleaning of a different stain, is also contemplated for the production of formulations suitable for cleaning a wide variety of stains. Additionally, the use of enzyme blends, in which each member of the blend possesses a different charge optimum, is contemplated in cases where the enzyme substrate itself undergoes charge changes during enzyme reaction Although described herein in relationship to proteases and blood, milk and ink stains, it is contemplated that the protease variants of the present invention are optimized for any enzyme-substrate interaction in any a variety of reaction media (i.e. conditions) dictated by the application e.g. cleaning applications.

As described in greater detail herein, the variant proteases of the present invention have important characteristics that make them very suitable for certain applications. For example, in some preferred embodiments, the variant proteases of the present invention have altered charge and/or hydrophobicity as compared to some currently used proteases. Thus, these proteases find particular use in cleaning compositions. Indeed, under certain wash conditions, the present proteases exhibit comparative or enhanced expression and/or stain removal activity as compared with currently used subtilisin proteases. Thus, it is contemplated that the cleaning and/or enzyme compositions of the present invention will be provided in a variety of cleaning compositions. Thus, the present proteases find use in various cleaning compositions, as well as animal feed applications, leather processing (e.g., bating), protein hydrolysis, and in textile uses. The identified proteases also find use in personal care applications.

Indeed, the protease variants of the present invention find use in a number of industrial applications, in particular within the cleaning, disinfecting, animal feed, and textile/leather industries. In some embodiments, the protease(s) of the present invention are combined with detergents, builders, bleaching agents and other conventional ingredients to produce a variety of novel cleaning compositions useful in the laundry and other cleaning arts such as, for example, laundry detergents (both powdered and liquid), laundry pre-soaks, all fabric bleaches, automatic dishwashing detergents (both liquid and powdered), household cleaners, particularly bar and liquid soap applications, and drain openers. In addition, the variant proteases find use in the cleaning of contact lenses, as well as other items, by contacting such materials with an aqueous solution of the cleaning composition. In addition these variant proteases can be used, for example in peptide hydrolysis, waste treatment, textile applications, medical device cleaning, biofilm removal and as fusion-cleavage enzymes in protein production, etc. The composition of these products is not critical to the present invention, as long as the variant protease(s) maintain their function in the setting used. In some embodiments, the compositions are readily prepared by combining a cleaning effective amount of the protease variant or an enzyme composition comprising the variant protease enzyme preparation with the conventional components of such compositions in their art recognized amounts.

Cleaning Compositions

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

As indicated herein, in some embodiments, the cleaning compositions of the present invention further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

The cleaning compositions of the present invention are advantageously employed for example, in laundry applications, hard surface cleaning, dishwashing applications, as well as cosmetic applications such as dentures, teeth, hair and skin. In addition, due to the unique advantages of increased effectiveness in lower temperature solutions, the enzymes of the present invention are ideally suited for laundry applications. Furthermore, the enzymes of the present invention find use in granular and liquid compositions.

The variant proteases of the present invention also find use cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the protease variants provided herein, alone or in combination with other proteases and/or additional enzymes. The required level of enzyme is achieved by the addition of one or more protease variants of the present invention. Typically the present cleaning compositions will comprise at least about 0.0001 weight percent, from about 0.0001 to about 10, from about 0.001 to about 1, or even from about 0.01 to about 0.1 weight percent of at least one of the variant proteases of the present invention.

The cleaning compositions herein are typically formulated such that, during use in aqueous cleaning operations, the wash water will have a pH of from about 5.0 to about 11.5 or even from about 7.5 to about 10.5. Liquid product formulations are typically formulated to have a neat pH from about 3.0 to about 9.0 or even from about 3 to about 5. Granular laundry products are typically formulated to have a pH from about 9 to about 11. Techniques for controlling pH at recommended usage levels include the use of buffers, alkalis, acids, etc., and are well known to those skilled in the art.

Suitable low pH cleaning compositions typically have a neat pH of from about 3 to about 5, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a neat pH of from about 3 to about 5. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the variant protease(s) is/are employed in a granular composition or liquid, it is desirable for the variant protease to be in the form of an encapsulated particle to protect the variant protease from other components of the granular composition during storage. In addition, encapsulation is also a means of controlling the availability of the variant protease during the cleaning process. In some embodiments, encapsulation enhances the performance of the variant protease(s) and/or additional enzymes. In this regard, the variant proteases of the present invention are encapsulated with any suitable encapsulating material known in the art. In some embodiments, the encapsulating material typically encapsulates at least part of the catalyst for the variant protease(s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the variant proteases of the present invention find particular use in the cleaning industry, including, but not limited to laundry and dish detergents. These applications place enzymes under various environmental stresses. The variant proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, European detergents typically have about 4500-5000 ppm of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present invention utilizes washing at temperatures from about 10° C. to about 40° C., or from about 10° C. to about 30° C., or from about 15° C. to about 25° C., as well as all other combinations within the range of about 10° C. to about 40° C. As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present invention provides variant proteases that show surprising wash performance in at least one set of wash conditions (e.g., water temperature, water hardness, and/or detergent concentration). In some embodiments, the variant proteases of the present invention are comparable in wash performance to other subtilisin proteases. In some embodiments, the variant proteases of the present invention exhibit enhanced wash performance as compared to subtilisin proteases currently commercially available. Thus, in some preferred embodiments of the present invention, the variant proteases provided herein exhibit enhanced oxidative stability, enhanced thermal stability, enhanced cleaning capabilities under various conditions, and/or enhanced chelator stability. In addition, the variant proteases of the present invention find use in cleaning compositions that do not include detergents, again either alone or in combination with builders and stabilizers.

In some embodiments of the present invention, the cleaning compositions comprise at least one variant protease of the present invention at a level from about 0.00001% to about 10% by weight of the composition and the balance (e.g., about 99.999% to about 90.0%) comprising cleaning adjunct materials by weight of composition. In other aspects of the present invention, the cleaning compositions of the present invention comprises at least one variant protease at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, hemicellulases, cellulases, peroxidases, proteases, xylanases, lipases, phospholipases, esterases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, a combination of enzymes is used (i.e., a "cocktail") comprising conventional applicable enzymes like protease, lipase, cutinase and/or cellulase in conjunction with amylase is used.

In addition to the protease variants provided herein, any other suitable protease finds use in the compositions of the present invention. Suitable proteases include those of animal, vegetable or microbial origin. In some particularly preferred embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the Fusarium protease described in WO 89/06270. In some embodiments, commercially available protease enzymes that find use in the present invention include, but are not limited to MAXATASE®, MAXACAL™, MAXAPEM™, OPTICLEAN®, OPTIMASE®, PROPERASE®, PURAFECT® PROPERASE®, EXCELLASE™, PURAFAST™, and PURAFECT® OXP (Genencor); ALCALASE®, SAVINASE®, PRIMASE®, DURAZYM™, POLARZYME®, OVOZYME®, LIQUANASE®, KANNASE®, NEUTRASE®, RELASE® and ESPERASE® (Novozymes); and BLAP™ (Henkel Kommanditgesellschaft auf Aktien, Duesseldorf, Germany. Various proteases are described in WO95/23221, WO 92/21760, U.S. Pat. Appln. Publ. No. 2008/0090747, and U.S. Pat. Nos. 5,801,039, 5,340,735, 5,500,364, 5,855,625, RE 34,606, 5,955,340, 5,700,676, 6,312,936, and 6,482,628, and various other patents. In some embodiments, metalloproteases find use in the present invention, including, but not limited to the neutral metalloprotease described in WO 07/044993.

In addition, any suitable lipase finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), *Pseudomonas* lipases such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 H9911), a *R. niveus* lipase (Kugimiya et al., Biosci. Biotech. Biochem. 56:716-719 [1992]) and *R. oryzae* lipase.

Other types of lipolytic enzymes such as cutinases also find use in some embodiments of the present invention, including but not limited to the cutinase derived from *Pseudomonas mendocina* (See, WO 88/09367), and the cutinase derived from *Fusarium solani pisi* (See, WO 90/09446).

Additional suitable lipases include commercially available lipases such as M1 LIPASE™, LUMA FAST™, and LIPOMAX™ (Genencor); LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In other aspects of the present invention, the cleaning compositions of the present invention also comprise lipases at a level of about 0.0001% to about 10%, about 0.001% to about 5%, about 0.001% to about 2%, about 0.005% to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296,839). Commercially available amylases that find use in the present invention include, but are not limited to DURAMYL®, TERMAMYL®, FUNGAMYL®, STAINZYME®, STAINZYME PLUS®, STAINZYME ULTRA®, NATALASE®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In other aspects of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME®, CAREZYME® (Novozymes), and KAC-500 (B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276). In some embodiments, the cleaning compositions of the present invention further comprise cellulases at a level from about 0.00001% to about 10% of additional cellulase by weight of the composition and the balance of cleaning adjunct materials by weight of composition. In other aspects of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114, 6,602,842, and 6,440,991, all of which are incorporated herein by reference). In some embodiments, the cleaning compositions of the present invention further comprise mannanases at a level from about 0.00001% to about 10% of additional mannanase by weight of the composition and the balance of cleaning adjunct materials by weight of composition. In other aspects of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In other aspects of the present invention, the cleaning compositions of the present invention also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some particularly preferred embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the variant protease(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracis, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

In some preferred embodiments, an effective amount of one or more variant protease(s) provided herein are included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the variant proteases of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458 find use with the variant proteases of the present invention. Thus, in some embodiments, the compositions comprising at least one variant protease of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one variant protease of the present invention are fabric cleaning compositions such as those described in U.S. Pat. Nos. 6,610,642 and 6,376,450. In addition, the variant proteases of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one variant protease provided herein. Thus, in some embodiments, the compositions comprising at least one variant protease of the present invention is a hard surface cleaning composition such as those described in U.S. Pat. Nos. 6,610, 642, 6,376,450, and 6,376,450.

In yet further embodiments, the present invention provides dishwashing compositions comprising at least one variant protease provided herein. Thus, in some embodiments, the compositions comprising at least one variant protease of the present invention is a hard surface cleaning composition such as those in U.S. Pat. Nos. 6,610,642 and 6,376,450. In some still further embodiments, the present invention provides dishwashing compositions comprising at least one variant protease provided herein. In some further embodiments, the compositions comprising at least one variant protease of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450, 6,605,458, 6,605,458, and 6,610,642, find use with the variant proteases provided herein.

The cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition is adjusted via the addition of a material such as monoethanolamine or an acidic material such as HCl.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the variant proteases of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, incorporated by reference. The aforementioned adjunct ingredients may constitute the balance of the cleaning compositions of the present invention.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some preferred embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some preferred embodiments, the anti-redeposition agent is a non-ionic surfactant as known in the art (See e.g., EP 2 100 949).

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some preferred embodiments, silicates are present at a level of from about 5% to about 15% by weight of the composition.

In some still additional embodiments, the cleaning compositions of the present invention also contain dispersants. Suitable water-soluble organic materials include, but are not limited to the homo-or co-polymeric acids or their salts, in which the polycarboxylic acid comprises at least two carboxyl radicals separated from each other by not more than two carbon atoms.

In some further embodiments, the enzymes used in the cleaning compositions are stabilized any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphaic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810410, WO 99/06521, and EP 2 100 949).

In some embodiments, the cleaning compositions of the present invention contain one or more catalytic metal complexes. In some embodiments, a metal-containing bleach catalyst finds use. In some preferred embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some preferred embodiments, provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include, but are not limited to manganese, iron and chromium. Preferred MRLs also include, but are not limited to special ultra-rigid ligands that are cross-bridged (e.g., 5,12-diethyl-1,5,8,12-tetraazabicyclo[6.6.2]hexadecane). Suitable transition metal MRLs are readily prepared by known procedures (See e.g., WO 2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

As indicated above, the cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,516,448, 5,489,392, and 5,486,303, all of which are incorporated herein by reference. In some embodiments in which a low pH cleaning composition is desired, the pH of such composition is adjusted via the addition of an acidic material such as HCl.

The cleaning compositions disclosed herein of find use in cleaning a situs (e.g., a surface, dishware, or fabric). Typically, at least a portion of the situs is contacted with an embodiment of the present cleaning composition, in neat form or diluted in a wash liquor, and then the situs is optionally washed and/or rinsed. For purposes of the present invention, "washing" includes but is not limited to, scrubbing, and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa and AA (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{405}$ (optical density at 405 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); LAS (lauryl sodium sulfonate); SDS (sodium dodecyl sulfate); Tris (tris(hydroxymethyl)aminomethane); TAED (N,N,N'N'-tetraacetylethylenediamine); BES (polyesstersulfone); MES (2-morpholinoethanesulfonic acid, monohydrate; f.w. 195.24; Sigma # M-3671); $CaCl_2$ (calcium chloride, anhydrous; f.w. 110.99; Sigma # C-4901); SRI (Stain Removal Index), BMI (blood milk ink) and BMI PI (blood milk ink performance index), TCA (tricholoroacetic acid) and TCA PI (tricholoroacetic acid performance index).

In addition materials were obtained from some of the following institutions: TIGR (The Institute for Genomic Research, Rockville, MD); AATCC (American Association of Textile and Coloring Chemists); Amersham (Amersham Life Science, Inc. Arlington Heights, Ill.); Corning (Corning International, Corning, N.Y.); ICN (ICN Pharmaceuticals, Inc., Costa Mesa, Calif.); Pierce (Pierce Biotechnology, Rockford, Ill.); Equest (Equest, Warwick International Group, Inc., Flintshire, UK); EMPA (Eidgenossische Material Prufungs and Versuch Anstalt, St. Gallen, Switzerland); CFT (Center for Test Materials, Vlaardingen, The Netherlands); Amicon (Amicon, Inc., Beverly, Mass.); ATCC (American Type Culture Collection, Manassas, Va.); Becton Dickinson (Becton Dickinson Labware, Lincoln Park, N.J.); Perkin-Elmer (Perkin-Elmer, Wellesley, Mass.); Rainin (Rainin Instrument, LLC, Woburn, Mass.); Eppendorf (Eppendorf AG, Hamburg, Germany); Waters (Waters, Inc., Milford, Mass.); Geneart (Geneart GmbH, Regensburg, Germany); Perseptive Biosystems (Perseptive Biosystems, Ramsey, Minn.); Molecular Probes (Molecular Probes, Eugene, Oreg.); BioRad (BioRad, Richmond, Calif.); Clontech (CLONTECH Laboratories, Palo Alto, Calif.); Cargill (Cargill, Inc., Minneapolis, Minn.); Difco (Difco Laboratories, Detroit, Mich.); GIBCO BRL or Gibco BRL (Life Technologies, Inc., Gaithersburg, Md.); New Brunswick (New Brunswick Scientific Company, Inc., Edison, N.J.); Thermoelectron (Thermoelectron Corp., Waltham, Mass.); BMG (BMG Labtech, GmbH, Offenburg, Germany); Greiner (Greiner Bio-One, Kremsmuenster, Austria); Novagen (Novagen, Inc., Madison, Wis.); Novex (Novex, San Diego, Calif.); Finnzymes (Finnzymes OY, Finland) Qiagen (Qiagen, Inc., Valencia, Calif.); Invitrogen (Invitrogen Corp., Carlsbad, Calif.); Sigma (Sigma Chemical Co., St. Louis, Mo.); DuPont Instruments (Asheville, N.Y.); Global Medical Instrumentation or GMI (Global Medical Instrumentation; Ramsey, Minn.); MJ Research (MJ Research, Waltham, Mass.); Infors (Infors AG, Bottmingen, Switzerland); Stratagene (Stratagene Cloning Systems, La Jolla, Calif.); Roche (Hoffmann La Roche, Inc., Nutley, N.J.); Agilent (Agilent Technologies, Palo Alto, Calif.); Merck (Merck & Co., Rahway, N.J.); Ion Beam Analysis Laboratory (Ion Bean Analysis Laboratory, The University of Surrey Ion Beam Centre (Guildford, UK); TOM (Terg-o-Meter); BMI (blood, milk, ink); BaChem (BaChem AG, Bubendorf, Switzerland); Molecular Devices (Molecular Devices, Inc., Sunnyvale, Calif.); Corning (Corning International, Corning, N.Y.); MicroCal (Microcal, Inc., Northhampton, Mass.); Chemical Computing (Chemical Computing Corp., Montreal, Canada); NCBI (National Center for Biotechnology Information); Beckman (Beckman-Coulter, Fullerton, Calif.); SeitzSchenk (SeitzSchenk Filtersystems GmbH, Bad Kreuznach, Germany); Pall (Pall Corp., East Hills, N.Y.); Malvern Instruments (Malvern Instruments, Inc., Worcestershire, UK), DNA 2.0 (Menlo Park, Calif.), Molecular Devices (Sunnyvale, Calif.), Costar (Cambridge, Mass.).

Example 1

Assays

In the following examples, various assays were used as set forth below for ease in reading. Any deviations from the protocols provided below are indicated.

A. TCA Assay for Protein Content Determination in 96-well Microliter Plates

For FNA (e.g., parent protease) and variants thereof, this assay was started using filtered culture supernatant from microtiter plates grown 3-4 days at 33 °C. with shaking at 230 rpm and humidified aeration. A fresh 96-well flat bottom microtiter plate (MTP) was used for the assay. First, 100 µL/well of 0.25 N HCl was placed in each well. Then, 50 µL of filtered culture broth was added. The light scattering/absorbance at 405 nm (use 5 sec mixing mode in the plate reader) was then determined, in order to provide the "blank" reading. For the test, 100 µL/well of 15% (w/v) trichloroacetic acid (TCA) was placed in the plates and incubated between 5 and 30 min at room temperature. The light scattering/absorbance at 405 nm (use 5 sec mixing mode in the plate reader) was then determined.

For GG36 (e.g., parent protease) and variants thereof, this assay was performed using filtered culture supernatant from microtiter plates grown approximately 3 days at 37° C. with shaking at 300 rpm and humidified aeration. In this assay 100 µL of a 0.25 M HCl solution was added to each well of a 96-well flat bottom microtiter plate. Subsequently, 25 µL aliquots of the filtered culture supernatants (containing the proteases) were added to wells. The light scattering/absorbance at 405 nm (using the 5 sec mixing mode in the plate reader) was then determined, in order to provide the "blank" reading. After this measurement, 100 µL of a 30% (w/v) TCA solution was added to each well and the microtiter plates were incubated between 5 and 15 minutes at room temperature. Finally, the resulting light scattering/absorbance at 405 nm (using the 5 sec mixing mode in the plate reader) was determined The equipment used was a Biomek FX Robot (Beckman Coulter) and a SpectraMAX (type 340; Molecular Devices) MTP Reader; the MTP's were from Costar (type 9017). The equipment used was a Biomek FX Robot (Beckman Coulter) and a SpectraMAX type 340 (Molecular Devices) MTP Reader; and the MTPs were type 9017 (Costar).

The calculations were performed by subtracting the blank (no TCA) from the test reading with TCA to provide a relative measure of the protein content in the samples. If desired, a standard curve can be created by calibrating the TCA readings with AAPF assays of clones with known conversion factors. However, the TCA results are linear with respect to protein concentration from 50 to 500 micrograms of protein per ml (ppm) and can thus be plotted directly against enzyme performance for the purpose of choosing good-performing variants. The turbidity/light scatter increase in the samples correlates to the total amount of precipitable protein in the culture supernatant.

B. Cleaning Performance Assays

The stain removal performance of reference serine proteases and variants thereof on microswatches was determined on a microtiter plate (MTP) scale in commercially available TIDE® 2X Cold detergent. Heat inactivated TIDE® 2X Cold (off-the-shelf detergent) in which lack of protease activity was confirmed was used in the assays. Heat inactivation of commercial detergent formulas serves to destroy the enzymatic activity of any protein components while retaining the properties of non-enzymatic components. Thus this method was suitable for preparing commercially purchased detergents for use in testing the enzyme variants of the present invention. The reagents used were: 5 mM HEPES, pH 8.0 or 5 mM MOPS, pH 7 buffer, 3:1 Ca: Mg for medium water hardness: ($CaCl_2$: $MgCl2.6H2O$); 15000 grains per gallon (gpg) stock diluted to 6 gpg. Two EMPA-116 BMI (blood/milk/ink) cotton swatches processed by CFT were used per well. The microswatches were pre-washed in deionised water for 20 minutes at ambient temperature. After the pre-washing step, the swatches were put on top of paper towels to dry. The air-dried swatches were then punched using a ¼" circular die on an expulsion press. Finally two microswatches were put into each well of a 96-well MTP vertically to expose the whole surface area (i.e. not flat on the bottom of the well). The working detergent solution is shown in Table 1-1.

TABLE 1-1

Working Detergent Solution

| Detergent | Temp (C.) | Detergent g/L | pH | Buffer | gpg | Protease |
|---|---|---|---|---|---|---|
| TIDE ® 2X Cold | 16 | 0.98 | 8 | 5 mM HEPES | 6 | FNA, GG36 |

The incubator was set 16° C. 10 µL samples from the master dilution plate of ~10 ppm enzyme was added to BMI 2-swatch plates with 190 µL working detergent solutions listed above. The volume was adjusted to give final concentration of 0.5 ppm for variants in the assay plates. The plates were immediately transferred to iEMS incubator/shaker (Thermo/Labsystems); and incubated for 30 minutes with 1400 rpm shaking at given temperature. Following incubation, 100 µL of supernatant was transferred into a new 96-well plate (Costar type 9017 used for reading reaction plates after incubation) and the absorbance was measured in SpectraMAX MTP Reader (type 340; Molecular Devices) at 405 nm and/or 600 nm. Control wells, containing 2 microswatches and detergent without the addition of protease samples were also included in the test. The measurement at 405 nm provides a higher value and tracks pigment removal, while the measurement at 600 nm tracks turbidity and cleaning. In this assay, the proteases hydrolyze the substrate and liberate pigment and insoluble particles from the substrate. Thus the rate of turbidity is a measure of enzyme activity.

Calculation of the Stain Removal Activity

The absorbance value obtained was corrected for the blank value (substrate without enzyme), providing a measure of hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme.

Performance Index

The performance index compares the performance of the variant (actual value) and the parent protease (theoretical value) at the same protein concentration. In addition, the theoretical values can be calculated, using the parameters of the binding curve (i.e., Langmuir equation) of the standard protease. A performance index (PI) that has a value >0.5 for at least one property identifies a variant comprising at least one mutation that can be combined with one or more mutations to generate proteins having appropriate performance indices for one or more properties of interest other than or in addition to the property of interest for which a PI value of >0.5 was measured.

Example 2

Bacillus subtilis GG36 Subtilisin Variants

In this example, experiments conducted to produce GG36 (also referred to herein as Bacillus lentus subtilisin) in B. subtilis are described. Transformation was performed as known in the art (See e.g., WO 02/14490).

GG36 Protease Production in Bacillus subtilis

The expression plasmid pAC-GG36ci was assembled using the GG36 codon-improved gene fused at the 8<sup>th</sup> codon of the aprE signal sequence under the control of the consensus aprE promoter and the BPN' transcriptional terminator. In the sequence provided below (SEQ ID NO:2), bold and italicized font indicates consensus aprE promoter, standard font indicates the signal sequence, underlined font indicates the pro sequence, and bold font indicates DNA that encodes GG36 mature protease, and underlined italicized font indicates BPN' terminator. The DNA sequence encoding the GG36 mature region (SEQ ID NO:4) is flanked by KpnI and XhoI restriction sites for cloning (see FIG. 4).

(SEQ ID NO: 2)
*atctcaaaaaaatgggtctactaaaatattact*

*ccatctattataataaattcacagaa*

*tagtcttttaagtaagtctactctgaattttttttaaaaggaga*

*gggtaaaga*gtgagaagcaaaaaattgtggatcgtcgcgtcgaccgca ttgctgatttctgttgcttttagctcatccatcgcatccgctgctgaa gaagcaaaagaaaaatatttaattggctttaatgagcaggaagctgtc agtgagtttgtagaacaagttgaggcaaatgacgaggtagccattctc tctgaggaagaggaagtcgaaattgaattgcttcatgaatttgaaacg attcctgttctgtccgttgagttaagcccagaagatgtggacgcgtta gagctcgatccagctatttcttatattgaagaggatgcagaagtaact aca atggcgcaatcggtaccatggggaattagcagagtacaagcccca gctgcacataaccgtggattgacaggttctggtgtaaaagttgctgtc cttgataccggtatttccactcatccagacttaaatattcgtggtgga gctagctttgtaccaggggaaccatccactcaagatggcaatggacat ggcactcatgttgccggcacaatcgcggctcttaacaattcaattggt gttcttggcgtagcgccaagcgcagaactatacgctgttaaagtatta ggagcaagcggttcaggctctgtcagctctattgcccaaggattggaa tgggcagggaacaatggcatgcacgttgctaatcttagtttaggatct ccttcgccaagtgccacacttgagcaagctgttaatagcgcgacttct agaggcgttcttgttgtagcggcctctggaaattcaggtgcaggctca atcagctatccggcccgttatgcgaacgctatggcagtcggagctact gaccaaaacaacaaccgcgccagcttttcacagtatggcgcagggctt gacattgtcgcaccaggtgtaaacgtgcagagcacttacccaggttca acatatgccagcttaaacggtacatcaatggctactcctcatgttgca ggtgcggctgcacttgttaaacaaaagaacccatcttggtccaatgta caaatccgcaatcatcttaagaatacggcaactagcttaggaagcaca aacttgtatggaagcggacttgtcaatgcagaagctgcaactcgttaa

*aagcttaactcgagataaaaaaccggccttggccccgccggtttttat*

The plasmid pAC-GG36ci shown in FIG. 4, was used for the expression of GG36 protease in B. subtilis. The plasmid elements are as follows: pUB 110=DNA fragment from plasmid pUB110 [McKenzie T., Hoshino T., Tanaka T., Sueoka N. (1986) The Nucleotide Sequence of pUB110: Some Salient Features in Relation to Replication and Its Regulation. Plasmid 15:93-103], pBR322=DNA fragment from plasmid pBR322 [Bolivar F, Rodriguez R L, Greene P J, Betlach M C, Heyneker H L, Boyer H W. (1977) Construction and characterization of new cloning vehicles. II. A multipurpose cloning system. Gene 2:95-113], pC194=DNA fragment from plasmid pC194 [Horinouchi S., Weisblum B. (1982) Nucleotide sequence and functional map of pC194, a plasmid that specifies inducible chloramphenicol resistance. J. Bacteriol 150: 815-825].

Plasmid features are as follows: Ori for B. subtilis=origin of replication from pUB110, CAT=chloramphenicol resistance gene from pC194, pMB1 origin=origin of replication from pBR322, bla=beta-lactamase from pBR322, Short aprE promoter=consensus transcriptional promoter, Signal Peptide=signal peptide, Pro Peptide=GG36 pro region, GG36ci Mature Peptide=mature GG36 (replaced by the coding regions for each variant expressed in this study), BPN' Terminator=transcriptional terminator from subtilisin BPN'.

The amino acid sequence of GG36 precursor protein is provided below (SEQ ID NO:3). In this sequence, bold indicates the mature GG36 protease (wildtype), which is also provided as SEQ ID NO:4:

(SEQ ID NO: 3)
MRSKKLWIVASTALLISVAFSSSIASAAEEAKEKYLIGFNEQEAVSEF

VEQVEANDEVAILSEEEEVEIELLHEFETIPVLSVELSPEDVDALELD

PAISYIEEDAEVTTMAQSVPWGISRVQAPAAHNRGLTGSGVKVAVLDT

```
GISTHPDLNIRGGASFVPGEPSTQDGNGHGTHVAGTIAALNNSIGVLG

VAPSAELYAVKVLGASGSGSVSSIAQGLEWAGNNGMHVANLSLGSPSP

SATLEQAVNSATSRGVLVVAASGNSGAGSISYPARYANAMAVGATDQN

NNRASFSQYGAGLDIVAPGVNVQSTYPGSTYASLNGTSMATPHVAGAA

ALVKQKNPSWSNVQIRNHLKNTATSLGSTNLYGSGLVNAEAATR*

(SEQ ID NO: 4)
AQSVPWGISRVQAPAAHNRGLTGSGVKVAVLDTGISTHPDLNIRGGAS

FVPGEPSTQDGNGHGTHVAGTIAALNNSIGVLGVAPSAELYAVKVLGA

SGSGSVSSIAQGLEWAGNNGMHVANLSLGSPSPSATLEQAVNSATSRG

VLVVAASGNSGAGSISYPARYANAMAVGATDQNNNRASFSQYGAGLDI

VAPGVNVQSTYPGSTYASLNGTSMATPHVAGAAALVKQKNPSWSNVQI

RNHLKNTATSLGSTNLYGSGLVNAEAATR*
```

Design and Generation of *Bacillus lentus* subtilisin (=GG36) Combinatorial Charge/Hydrophobic Library (CCHL)

The *Bacillus lentus* subtilisin combinatorial charge/hydrophobicity library (CCHL) was designed by identifying seven well-distributed, surface-exposed amino-acids. These residues are S24, R45, S101, Q109, G118, T213, and L217. The number of the position of the substitution is by correspondence to the enumerated position in the BPN' subtilisin (BPN' numbering; FIG. 1). A 33-member combinatorial hydrophobic library (GH2-GH33) was created by making combinations of four possibilities at each site: wild-type, glutamine (Q), glutamic acid (E), leucine (L) and arginine (R) as shown in Table 2-1.

The pAC-GG36ci plasmid containing the codon-improved GG36 gene was sent to DNA 2.0 Inc. (Menlo Park, Calif.) for the generation of the CHL. The *Bacillus subtilis* strain (genotype: ΔaprE, ΔnprE, ΔspoIIE, amyE::xylRPxylAcomK-phleo) was provided as the host strain for the transformation of the DNA encoding the GG36 variant subtilisins. Variants were supplied as glycerol stocks in 96-well plates.

Table 2-2 shows the substitutions made in GG36 to create the variants. Table 2-1 also provides the difference in net charge and hydrophobicity between the variant GG36 and the wild-type.

Expression of Protease Variants

*Bacillus subtilis* clones containing GG36 or FNA expression vectors were replicated with a steel 96-well replicator from glycerol stocks into 96-well culture plates (BD, 353075) containing 200 μl of LB media+25 μg/ml chloramphenicol, grown overnight at 37° C., 220 rpm in a humidified enclosure. 200 μl from the overnight culture was used to inoculate 2000 μl defined media+25 μg/ml chloramphenicol in 5 ml plastic shake tubes. The cultivation media was an enriched semi-defined media based on MOPs buffer, with urea as major nitrogen source, glucose as the main carbon source, and supplemented with 1% soytone for robust cell growth. Shake tubes were incubated at 37° C., 220 rpm, for 60 hours. Following 60 hours, supernatants spun down in a centrifuge at greater than 8000×RCF. Solution was decanted into 15 ml polypropylene conical tubes for storage. No further purification or concentration was performed. Supernatant stocks were formulated to 40% propylene glycol for long-term stability and stored at 4° C.

TABLE 2-1

GG36 Combinatorial Charge/Hydrophobicity Library.

| Variant # | S24 | R45 | S101 | Q109 | G118 | T213 | L217 | Variant | Net Charge Change Relative to GG36 | Kyte-Doolitle Hydrophobicity Change relative to GG36 |
|---|---|---|---|---|---|---|---|---|---|---|
| GG36 | S24S | R45R | S101S | Q109Q | G118G | T213T | L217L | S24S-R45R-S101S-Q109Q-G118G-T213T-L217L | 0 | 0 |
| GH-2 | S24Q | R45Q | S101Q | Q109Q | G118Q | T213Q | L217L | S24Q-R45Q-S101Q-Q109Q-G118Q-T213Q-L217L | −1 | −10.3 |
| GH-3 | S24S | R45Q | S101Q | Q109Q | G118Q | T213Q | L217L | S24S-R45Q-S101Q-Q109Q-G118Q-T213Q-L217L | −1 | −7.6 |
| GH-4 | S24S | R45R | S101Q | Q109Q | G118Q | T213Q | L217L | S24S-R45R-S101Q-Q109Q-G118Q-T213Q-L217L | 0 | −8.6 |
| GH-5 | S24S | R45R | S101S | Q109Q | G118Q | T213Q | L217L | S24S-R45R-S101S-Q109Q-G118Q-T213Q-L217L | 0 | −5.9 |
| GH-6 | S24S | R45R | S101S | Q109Q | G118Q | T213Q | L217L | S24S-R45R-S101S-Q109Q-G118Q-T213Q-L217L | 0 | −5.9 |
| GH-7 | S24S | R45R | S101S | Q109Q | G118G | T213Q | L217L | S24S-R45R-S101S-Q109Q-G118G-T213Q-L217L | 0 | −2.8 |
| GH-8 | S24E | R45Q | S101Q | Q109Q | G118Q | T213Q | L217L | S24E-R45Q-S101Q-Q109Q-G118Q-T213Q-L217L | −2 | −10.3 |
| GH-9 | S24E | R45E | S101Q | Q109Q | G118Q | T213Q | L217L | S24E-R45E-S101Q-Q109Q-G118Q-T213Q-L217L | −3 | −10.3 |
| GH-10 | S24E | R45E | S101E | Q109Q | G118Q | T213Q | L217L | S24E-R45E-S101E-Q109Q-G118Q-T213Q-L217L | −4 | −10.3 |
| GH-11 | S24E | R45E | S101E | Q109E | G118Q | T213Q | L217L | S24E-R45E-S101E-Q109E-G118Q-T213Q-L217L | −5 | −10.3 |
| GH-12 | S24E | R45E | S101E | Q109E | G118E | T213Q | L217L | S24E-R45E-S101E-Q109E-G118E-T213Q-L217L | −6 | −10.3 |
| GH-13 | S24E | R45E | S101E | Q109E | G118E | T213E | L217L | S24E-R45E-S101E-Q109E-G118E-T213E-L217L | −7 | −10.3 |
| GH-14 | S24L | R45Q | S101Q | Q109Q | G118Q | T213Q | L217L | S24L-R45Q-S101Q-Q109Q-G118Q-T213Q-L217L | −1 | −3 |
| GH-15 | S24L | R45L | S101Q | Q109Q | G118Q | T213Q | L217L | S24L-R45L-S101Q-Q109Q-G118Q-T213Q-L217L | −1 | 4.3 |
| GH-16 | S24L | R45L | S101L | Q109Q | G118Q | T213Q | L217L | S24L-R45L-S101L-Q109Q-G118Q-T213Q-L217L | −1 | 11.6 |

TABLE 2-1-continued

GG36 Combinatorial Charge/Hydrophobicity Library.

| Variant # | S24 | R45 | S101 | Q109 | G118 | T213 | L217 | Variant | Net Charge Change Relative to GG36 | Kyte-Doolitle Hydrophobicity Change relative to GG36 |
|---|---|---|---|---|---|---|---|---|---|---|
| GH-17 | S24L | R45L | S101L | Q109L | G118Q | T213Q | L217L | S24L-R45L-S101L-Q109L-G118Q-T213Q-L217L | −1 | 18.9 |
| GH-18 | S24L | R45L | S101L | Q109L | G118L | T213Q | L217L | S24L-R45L-S101L-Q109L-G118L-T213Q-L217L | −1 | 26.2 |
| GH-19 | S24L | R45L | S101L | Q109L | G118L | T213L | L217L | S24L-R45L-S101L-Q109L-G118L-T213L-L217L | −1 | 33.5 |
| GH-20 | S24R | R45Q | S101Q | Q109Q | G118Q | T213Q | L217L | S24R-R45Q-S101Q-Q109Q-G118Q-T213Q-L217L | 0 | −11.3 |
| GH-21 | S24R | R45R | S101Q | Q109Q | G118Q | T213Q | L217L | S24R-R45R-S101Q-Q109Q-G118Q-T213Q-L217L | 1 | −12.3 |
| GH-22 | S24R | R45R | S101R | Q109Q | G118Q | T213Q | L217L | S24R-R45R-S101R-Q109Q-G118Q-T213Q-L217L | 2 | −13.3 |
| GH-23 | S24R | R45R | S101R | Q109R | G118Q | T213Q | L217L | S24R-R45R-S101R-Q109R-G118Q-T213Q-L217L | 3 | −14.3 |
| GH-24 | S24R | R45R | S101R | Q109R | G118R | T213Q | L217L | S24R-R45R-S101R-Q109R-G118R-T213Q-L217L | 4 | −15.3 |
| GH-25 | S24R | R45R | S101R | Q109R | G118R | T213R | L217L | S24R-R45R-S101R-Q109R-G118R-T213R-L217L | 5 | −16.3 |
| GH-26 | S24E | R45R | S101R | Q109R | G118R | T213R | L217L | S24E-R45R-S101R-Q109R-G118R-T213R-L217L | 3 | −15.3 |
| GH-27 | S24E | R45E | S101R | Q109R | G118R | T213R | L217L | S24E-R45E-S101R-Q109R-G118R-T213R-L217L | 1 | −14.3 |
| GH-28 | S24E | R45E | S101E | Q109R | G118R | T213R | L217L | S24E-R45E-S101E-Q109R-G118R-T213R-L217L | −1 | −13.3 |
| GH-29 | S24E | R45E | S101E | Q109E | G118R | T213R | L217L | S24E-R45E-S101E-Q109E-G118R-T213R-L217L | −3 | −12.3 |
| GH-30 | S24E | R45E | S101E | Q109E | G118E | T213R | L217L | S24E-R45E-S101E-Q109E-G118E-T213R-L217L | −5 | −11.3 |
| GH-31 | S24E | R45E | S101E | Q109E | G118E | T213E | L217L | S24E-R45E-S101E-Q109E-G118E-T213E-L217L | −7 | −10.3 |
| GH-32 | S24Q | R45Q | S101Q | Q109Q | G118Q | T213Q | L217Q | S24Q-R45Q-S101Q-Q109Q-G118Q-T213Q-L217Q | −1 | −17.6 |
| GH-33 | S24Q | R45Q | S101Q | Q109Q | G118Q | T213Q | L217E | S24Q-R45Q-S101Q-Q109Q-G118Q-T213Q-L217E | −2 | −17.6 |

Mutations are Listed According to BPN' Numbering. Charge/Hydrophobicity Changes were Calculated Relative to GG36.

Example 3

Bacillus subtilis FNA Subtilisin Variants

FNA Protease Production in B. subtilis

In this example, experiments conducted to produce FNA (also referred to herein as Bacillus subtilis subtilisin BPN'-Y217L (=FNA)) in B. subtilis are described. Transformation was performed as known in the art (See e.g., WO 02/14490).

The expression plasmid pAC-FNAre was assembled using the FNA gene, fused at the 8$^{th}$ codon of the aprE signal sequence, under the control of the consensus aprE promoter and BPN' transcriptional terminator. In the sequence provided below (SEQ ID NO:5), bold and italicized font indicates consensus aprE promoter, standard font indicates the signal sequence, underlined font indicates the pro sequence, bold font indicates DNA that encodes FNA mature protease, and underlined italicized font indicates BPN' terminator. The FNA mature region contains the KpnI and XhoI restriction sites for cloning (see FIG. 5).

(SEQ ID NO: 5)
*gaattcatctcaaaaaaatgggtctac*

*taaatattattccatctattata*

*ataaattcacagaatagtcttttaagt*

*aagtctactctgaattttttaaaaggagagggtaaaga*gtgag aagcaaaaaattgtggatcagtttgctgtttgctttagcgttaatctt tacgatggcgttcggcagcacatccagcgcgcaggct<u>gcagggaaatc</u>

<u>aaacgggaaaagaaatatattgtcgggtttaaacagacaatgagcac</u>

<u>gatgagcgccgctaagaagaaagacgtcatttctgaaaaaggcgggaa</u>

<u>agtgcaaaagcaattcaaatatgtagacgcagctagcgctacattaaa</u>

<u>cgaaaaagctgtaaaagaattgaaaaaagacccgagcgtcgcttacgt</u>

<u>tgaagaagatcacgtagcacacgcgtac</u>gcgcagtccgtgccatatgg cgtatcacaaattaaagcccctgctctgcactctcaaggctacaccgg ttcaaatgttaaagtagcggttatcgacagcggtatcgattcttctca tccagatcttaaagtagcaggcggagccagcatggttccttctgaaac aaatcctttccaagacaacaactctcacggaacacacgttgctggtac cgttgcggctcttaataactcaatcggtgtattaggcgttgcgccaag cgcatcactttacgctgtaaaagttctcggcgccgacggttccggcca atacagctggatcattaacggaatcgagtgggcgatcgcaaacaatat ggacgttattaacatgagcctcggcggaccgtccggttctgctgcttt

-continued

```
aaaagcggcagttgataaagccgttgcatccggcgtcgtagtcgttgc ggcagccggcaacgaaggcacttccggcagctcaagcacagtgggcta ccctggtaaataccttctgtcattgcagtaggcgctgtcgacagcag caaccaaagagcatctttctcaagcgtaggacctgagctcgatgtcat ggcacctggcgtatctatccaaagcacgcttcctggaaacaaatacgg cgcgttgaacggtacatcaatggcatctccgcacgttgccggagccgc ggctttgattctttctaagcacccgaactggacaaacactcaagtccg cagctctctagaaaacaccactacaaaacttggtgattctttctacta tggaaaagggctgatcaatgtacaggcggcagctcagtaaaactcgag ataaaaaccggccttggccccgccggtttttttat.
```

Figure 5:
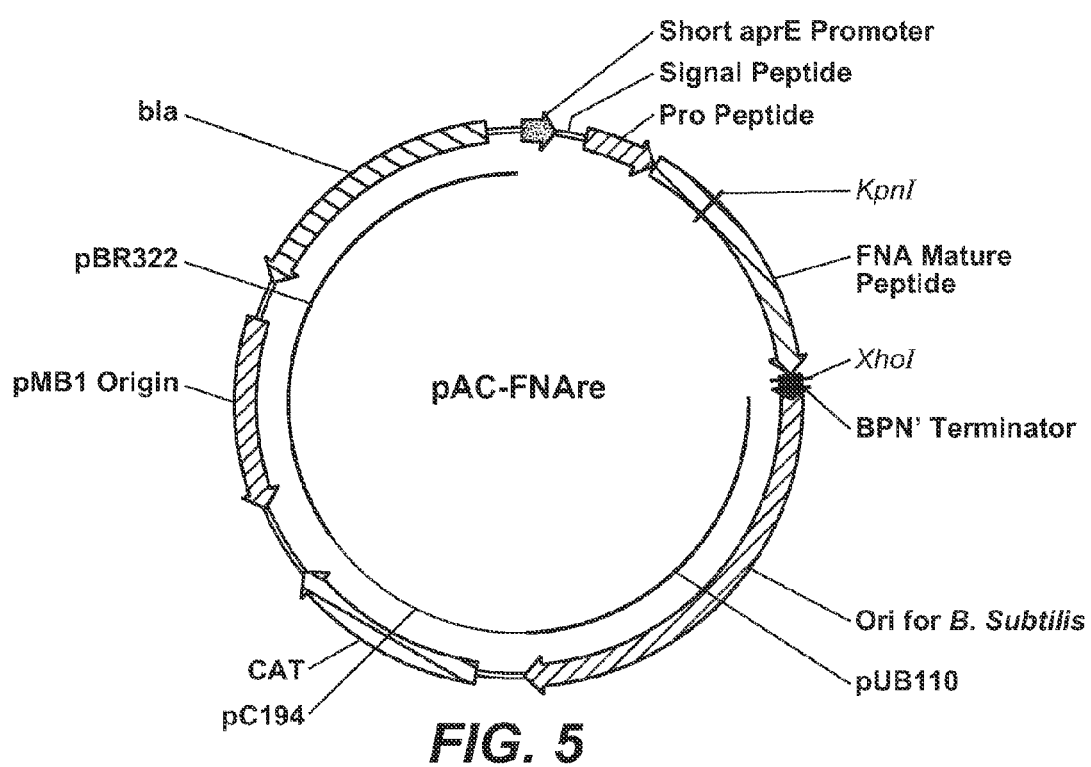
FIG. 5 provides a map of pAC-FNAre.

The plasmid pAC-FNAre as shown in FIG. 5, was used for the expression of FNA protease in *B. subtilis*. The plasmid elements are as follows: pUB110=DNA fragment from plasmid pUB110 [McKenzie T., Hoshino T., Tanaka T., Sueoka N. (1986) The Nucleotide Sequence of pUB110: Some Salient Features in Relation to Replication and Its Regulation. Plasmid 15:93-103], pBR322=DNA fragment from plasmid pBR322 [Bolivar F, Rodriguez R L, Greene P J, Betlach M C, Heyneker H L, Boyer H W. (1977) Construction and characterization of new cloning vehicles. II. A multipurpose cloning system. Gene 2:95-113], pC194 =DNA fragment from plasmid pC194 [Horinouchi S., Weisblum B. (1982) Nucleotide sequence and functional map of pC194, a plasmid that specifies inducible chloramphenicol resistance. J. Bacteriol 150: 815-825].

Plasmid features are as follows: Ori for *B. subtilis*=origin of replication from pUB 110, CAT=chloramphenicol resistance gene from pC194, pMB1 origin=origin of replication from pBR322, bla=beta-lactamase from pBR322, Short aprE promoter=consensus transcriptional promoter, Signal Peptide=signal peptide [specify], Pro Peptide=FNA pro region, FNA Mature Peptide=mature FNA (replaced by the coding regions for each variant expressed in this study), BPN' Terminator=transcriptional terminator from subtilisin BPN'.

The amino acid sequence of FNA precursor protein is provided below (SEQ ID NO:6). In this sequence, bold indicates the mature FNA protease (wildtype), which is also provided as SEQ ID NO:7.

(SEQ ID NO: 6)
MRSKKLWISLLFALALIFTMAFGSTSSAQAAGKSNGEKKYIVGFKQTM

STMSAAKKKDVISEKGGKVQKQFKYVDAASATLNEKAVKELKKDPSVA

YVEEDHVAHAYAQSVPYGVSQIKAPALHSQGYTGSNVKVAVIDSGIDS

SHPDLKVAGGASMVPSETNPFQDNNSHGTHVAGTVAALNNSIGVLGVA

PSASLYAVKVLGADGSGQYSWIINGIEWAIANNMDVINMSLGGPSGSA

ALKAAVDKAVASGVVVVAAAGNEGTSGSSSTVGYPGKYPSVIAVGAVD

SSNQRASFSSVGPELDVMAPGVSIQSTLPGNKYGALNGTSMASPHVAG

AAALILSKHPNWTNTQVRSSLENTTTKLGDSFYYGKGLINVQAAAQ*

(SEQ ID NO: 7)
AQSVPYGVSQIKAPALHSQGYTGSNVKVAVIDSGIDSSHPDLKVAGGA

SMVPSETNPFQDNNSHGTHVAGTVAALNNSIGVLGVAPSASLYAVKVL

GADGSGQYSWIINGIEWAIANNMDVINMSLGGPSGSAALKAAVDKAVA

SGVVVVAAAGNEGTSGSSSTVGYPGKYPSVIAVGAVDSSNQRASFSSV

GPELDVMAPGVSIQSTLPGNKYGALNGTSMASPHVAGAAALILSKHPN

WTNTQVRSSLENTTTKLGDSFYYGKGLINVQAAAQ*

Design and Generation of subtilisin BPN'-Y217L (=FNA) Combinatorial Charge/Hydrophobic Libraries (CHL)

The subtilisin BPN'-Y217L combinatorial charge hydrophobic library was designed by identifying seven well-distributed, surface-exposed amino acids. These residues are S24, A45, S101, N109, N118, K213, and L217. A 32-member combinatorial hydrophobic library (FH2-FH33) was created by making combinations of four possibilities at each site: wild-type, glutamine (Q), glutamic acid (E), leucine (L) and arginine (R) as shown in Table 3-1 .

The pAC-FNAre plasmid containing the FNA gene was sent to DNA 2.0 Inc. (Menlo Park, Calif.) for the generation of the Combinatorial Hydrophobic Libraries. The *Bacillus subtilis* strain (genotype: ΔaprE, ΔnprE, ΔspoIIE, amyE::xylR-PxylAcomK-phleo) was provided for the transformations of the DNA encoding the FNA variant substitutions. Variants were supplied as glycerol stocks in 96-well plates.

Table 3-1 shows the substitutions made in FNA to create the variants. Table 3-1 also provides the difference in net charge and hydrophobicity between the variant FNA and the wild-type.

Expression of Protease Variants

*Bacillus subtilis* clones containing GG36 or FNA expression vectors were replicated with a steel 96-well replicator from glycerol stocks into 96-well culture plates (Becton Dickinson, 353075) containing 200 μl of LB media+25 μg/ml chloramphenicol, grown overnight at 37° C., 220 rpm in a humidified enclosure. 200 μl from the overnight culture was used to inoculate 2000 μl defined media+25 μg/ml chloramphenicol in 5 ml plastic shake tubes. The cultivation media was an enriched semi-defined media based on MOPs buffer, with urea as major nitrogen source, glucose as the main carbon source, and supplemented with 1% soytone for robust cell growth. Shake tubes were incubated at 37° C., 220 rpm, for 60 hours. Following 60 hours, supernatants spun down in a centrifuge at greater than 8000×RCF. Solution was decanted into 15 ml polypropylene conical tubes for storage. No further purification or concentration was performed. Supernatant stocks were formulated to 40% propylene glycol for long-term stability and stored at

TABLE 3-1

FNA Combinatorial Charge/Hydrophobicity Library.

| Variant # | S24 | A45 | S101 | N109 | N118 | K213 | L217 | Variant | Net Charge Change Relative to FNA | Kyte-Doolitle Hydrophobicity Change relative to FNA |
|---|---|---|---|---|---|---|---|---|---|---|
| FNA | S24S | A45A | S101S | N109N | N118N | K213K | L217L | S24S-A45A-S101S-N109N-N118N-K213K-L217L | 0 | 0 |
| FH-2 | S24Q | A45Q | S101Q | N109Q | N118Q | K213Q | L217L | S24Q-A45Q-S101Q-N109Q-N118Q-K213Q-L217L | −1 | −10.3 |
| FH-3 | S24S | A45Q | S101Q | N109Q | N118Q | K213Q | L217L | S24S-A45Q-S101Q-N109Q-N118Q-K213Q-L217L | −1 | −7.6 |
| FH-4 | S24S | A45A | S101Q | N109Q | N118Q | K213Q | L217L | S24S-A45A-S101Q-N109Q-N118Q-K213Q-L217L | −1 | −2.3 |
| FH-5 | S24S | A45A | S101S | N109Q | N118Q | K213Q | L217L | S24S-A45A-S101S-N109Q-N118Q-K213Q-L217L | −1 | 0.4 |
| FH-6 | S24S | A45A | S101S | N109N | N118Q | K213Q | L217L | S24S-A45A-S101S-N109N-N118Q-K213Q-L217L | −1 | 0.4 |
| FH-7 | S24S | A45A | S101S | N109N | N118N | K213Q | L217L | S24S-A45A-S101S-N109N-N118N-K213Q-L217L | −1 | 0.4 |
| FH-8 | S24E | A45Q | S101Q | N109Q | N118Q | K213Q | L217L | S24E-A45Q-S101Q-N109Q-N118Q-K213Q-L217L | −2 | −10.3 |
| FH-9 | S24E | A45E | S101Q | N109Q | N118Q | K213Q | L217L | S24E-A45E-S101Q-N109Q-N118Q-K213Q-L217L | −3 | −10.3 |
| FH-10 | S24E | A45E | S101E | N109Q | N118Q | K213Q | L217L | S24E-A45E-S101E-N109Q-N118Q-K213Q-L217L | −4 | −10.3 |
| FH-11 | S24E | A45E | S101E | N109E | N118Q | K213Q | L217L | S24E-A45E-S101E-N109E-N118Q-K213Q-L217L | −5 | −10.3 |
| FH-12 | S24E | A45E | S101E | N109E | N118E | K213Q | L217L | S24E-A45E-S101E-N109E-N118E-K213Q-L217L | −6 | −10.3 |
| FH-13 | S24E | A45E | S101E | N109E | N118E | K213E | L217L | S24E-A45E-S101E-N109E-N118E-K213E-L217L | −7 | −10.3 |
| FH-14 | S24L | A45Q | S101Q | N109Q | N118Q | K213Q | L217L | S24L-A45Q-S101Q-N109Q-N118Q-K213Q-L217L | −1 | −3 |
| FH-15 | S24L | A45L | S101Q | N109Q | N118Q | K213Q | L217L | S24L-A45L-S101Q-N109Q-N118Q-K213Q-L217L | −1 | 4.3 |
| FH-16 | S24L | A45L | S101L | N109Q | N118Q | K213Q | L217L | S24L-A45L-S101L-N109Q-N118Q-K213Q-L217L | −1 | 11.6 |
| FH-17 | S24L | A45L | S101L | N109L | N118Q | K213Q | L217L | S24L-A45L-S101L-N109L-N118Q-K213Q-L217L | −1 | 18.9 |
| FH-18 | S24L | A45L | S101L | N109L | N118L | K213Q | L217L | S24L-A45L-S101L-N109L-N118L-K213Q-L217L | −1 | 26.2 |
| FH-19 | S24L | A45L | S101L | N109L | N118L | K213L | L217L | S24L-A45L-S101L-N109L-N118L-K213L-L217L | −1 | 33.5 |
| FH-20 | S24R | A45Q | S101Q | N109Q | N118Q | K213Q | L217L | S24R-A45Q-S101Q-N109Q-N118Q-K213Q-L217L | 0 | −11.3 |
| FH-21 | S24R | A45R | S101Q | N109Q | N118Q | K213Q | L217L | S24R-A45R-S101Q-N109Q-N118Q-K213Q-L217L | 1 | −12.3 |
| FH-22 | S24R | A45R | S101R | N109Q | N118Q | K213Q | L217L | S24R-A45R-S101R-N109Q-N118Q-K213Q-L217L | 2 | −13.3 |
| FH-23 | S24R | A45R | S101R | N109R | N118Q | K213Q | L217L | S24R-A45R-S101R-N109R-N118Q-K213Q-L217L | 3 | −14.3 |
| FH-24 | S24R | A45R | S101R | N109R | N118R | K213Q | L217L | S24R-A45R-S101R-N109R-N118R-K213Q-L217L | 4 | −15.3 |
| FH-25 | S24R | A45R | S101R | N109R | N118R | K213R | L217L | S24R-A45R-S101R-N109R-N118R-K213R-L217L | 5 | −16.3 |
| FH-26 | S24E | A45R | S101R | N109R | N118R | K213R | L217L | S24E-A45R-S101R-N109R-N118R-K213R-L217L | 3 | −15.3 |
| FH-27 | S24E | A45E | S101R | N109R | N118R | K213R | L217L | S24E-A45E-S101R-N109R-N118R-K213R-L217L | 1 | −14.3 |
| FH-28 | S24E | A45E | S101E | N109R | N118R | K213R | L217L | S24E-A45E-S101E-N109R-N118R-K213R-L217L | −1 | −13.3 |
| FH-29 | S24E | A45E | S101E | N109E | N118R | K213R | L217L | S24E-A45E-S101E-N109E-N118R-K213R-L217L | −3 | −12.3 |
| FH-30 | S24E | A45E | S101E | N109E | N118E | K213R | L217L | S24E-A45E-S101E-N109E-N118E-K213R-L217L | −5 | −11.3 |
| FH-31 | S24E | A45E | S101E | N109E | N118E | K213E | L217L | S24E-A45E-S101E-N109E-N118E-K213E-L217L | −7 | −10.3 |
| FH-32 | S24Q | A45Q | S101Q | N109Q | N118Q | K213Q | L217Q | S24Q-A45Q-S101Q-N109Q-N118Q-K213Q-L217Q | −1 | −17.6 |
| FH-33 | S24Q | A45Q | S101Q | N109Q | N118Q | K213Q | L217E | S24Q-A45Q-S101Q-N109Q-N118Q-K213Q-L217E | −2 | −17.6 |

Mutations are listed according to BPN' numbering. Charge/Hydrophobicity changes were calculated relative to FNA.

Example 4

Evaluation of Stain Removal and Relative Expression

This Example describes the testing of GG36 and FNA combinatorial hydrophobic library variants in a BMI microswatch assay. The methods provided in Example 1 were used. The results shown in Tables 4-1 (GG36), and 4-2 (FNA) are performance indices in which the performance of the variant is compared to the respective parent for relative protein expression (TCA PI) and stain removal activity (BMI PI). Those variants with a performance index greater than 0.5 (PI >0.5) have improved performance. Performance index less than or equal to 0.05 were set at 0.05 and are indicated in bold italics. ND indicates not determined.

TABLE 4-1

Relative Expression and Stain Removal Performance of GG36 Combinatorial/Charge Hydrophobicity Library Variants. Mutations are Listed According to BPN' Numbering. Performance Index and Charge/Hydrophobicity Changes Calculated Relative to GG36 (parent)

| Variant # | Variant | Net Charge Change Relative to GG36 | Kyte-Doolitle Hydrophobicity Change relative to GG36 | TCA PI | BMI PI |
|---|---|---|---|---|---|
| GG36 | S24S- R45R- S101S- Q109Q- G118G- T213T- L217L | 0 | 0 | 1.00 | 1.00 |
| GH-2 | S24Q- R45Q- S101Q- Q109Q- G118Q- T213Q- L217L | −1 | −10.3 | 1.03 | 0.06 |
| GH-3 | S24S- R45Q- S101Q- Q109Q- G118Q- T213Q- L217L | −1 | −7.6 | 1.05 | 0.42 |
| GH-4 | S24S- R45R- S101Q- Q109Q- G118Q- T213Q- L217L | 0 | −8.6 | 0.87 | 0.23 |
| GH-5 | S24S- R45R- S101S- Q109Q- G118Q- T213Q- L217L | 0 | −5.9 | 1.00 | 0.05 |
| GH-6 | S24S- R45R- S101S- Q109Q- G118Q- T213Q- L217L | 0 | −5.9 | ND | ND |
| GH-7 | S24S- R45R- S101S- Q109Q- G118G- T213Q- L217L | 0 | −2.8 | 0.79 | 0.38 |
| GH-8 | S24E- R45Q- S101Q- Q109Q- G118Q- T213Q- L217L | −2 | −10.3 | 1.01 | 0.47 |
| GH-9 | S24E- R45E- S101Q- Q109Q- G118Q- T213Q- L217L | −3 | −10.3 | 0.89 | 0.26 |
| GH-10 | S24E- R45E- S101E- Q109Q- G118Q- T213Q- L217L | −4 | −10.3 | 1.28 | 0.04 |
| GH-11 | S24E- R45E- S101E- Q109E- G118Q- T213Q- L217L | −5 | −10.3 | 1.09 | 0.78 |
| GH-12 | S24E- R45E- S101E- Q109E- G118E- T213Q- L217L | −6 | −10.3 | 1.10 | 0.29 |
| GH-13 | S24E- R45E- S101E- Q109E- G118E- T213E- L217L | −7 | −10.3 | 1.06 | 0.71 |
| GH-14 | S24L- R45Q- S101Q- Q109Q- G118Q- T213Q- L217L | −1 | −3 | 0.96 | 0.37 |
| GH-15 | S24L- R45L- S101Q- Q109Q- G118Q- T213Q- L217L | −1 | 4.3 | 0.99 | 0.52 |
| GH-16 | S24L- R45L- S101L- Q109Q- G118Q- T213Q- L217L | −1 | 11.6 | 0.88 | 0.08 |
| GH-17 | S24L- R45L- S101L- Q109L- G118Q- T213Q- L217L | −1 | 18.9 | 0.90 | 0.40 |
| GH-18 | S24L- R45L- S101L- Q109L- G118L- T213Q- L217L | −1 | 26.2 | 0.96 | 0.09 |
| GH-19 | S24L- R45L- S101L- Q109L- G118L- T213L- L217L | −1 | 33.5 | 1.06 | *0.05* |
| GH-20 | S24R- R45Q- S101Q- Q109Q- G118Q- T213Q- L217L | 0 | −11.3 | 1.05 | 0.56 |
| GH-21 | S24R- R45R- S101Q- Q109Q- G118Q- T213Q- L217L | 1 | −12.3 | 0.78 | 0.21 |
| GH-22 | S24R- R45R- S101R- Q109Q- G118Q- T213Q- L217L | 2 | −13.3 | 0.74 | 0.19 |
| GH-23 | S24R- R45R- S101R- Q109R- G118Q- T213Q- L217L | 3 | −14.3 | 0.75 | 0.15 |
| GH-24 | S24R- R45R- S101R- Q109R- G118R- T213Q- L217L | 4 | −15.3 | 0.68 | 0.07 |
| GH-25 | S24R- R45R- S101R- Q109R- G118R- T213R- L217L | 5 | −16.3 | 1.09 | *0.05* |
| GH-26 | S24E- R45R- S101R- Q109R- G118R- T213R- L217L | 3 | −15.3 | 0.90 | *0.05* |
| GH-27 | S24E- R45E- S101R- Q109R- G118R- T213R- L217L | 1 | −14.3 | 0.79 | *0.05* |
| GH-28 | S24E- R45E- S101E- Q109R- G118R- T213R- L217L | −1 | −13.3 | 0.87 | 0.06 |
| GH-29 | S24E- R45E- S101E- Q109E- G118R- T213R- L217L | −3 | −12.3 | 0.92 | 0.31 |

TABLE 4-1-continued

Relative Expression and Stain Removal Performance of GG36 Combinatorial/Charge Hydrophobicity Library Variants. Mutations are Listed According to BPN' Numbering. Performance Index and Charge/Hydrophobicity Changes Calculated Relative to GG36 (parent)

| Variant # | Variant | Net Charge Change Relative to GG36 | Kyte-Doolitle Hydrophobicity Change relative to GG36 | TCA PI | BMI PI |
|---|---|---|---|---|---|
| GH-30 | S24E- R45E- S101E- Q109E- G118E- T213R- L217L | −5 | −11.3 | 0.93 | 0.47 |
| GH-31 | S24E- R45E- S101E- Q109E- G118E- T213E- L217L | −7 | −10.3 | 1.01 | 0.40 |
| GH-32 | S24Q- R45Q- S101Q- Q109Q- G118Q- T213Q- L217Q | −1 | −17.6 | 1.10 | 0.07 |
| GH-33 | S24Q- R45Q- S101Q- Q109Q- G118Q- T213Q- L217E | −2 | −17.6 | 1.11 | 0.47 |

TABLE 4-2

Relative Expression and Stain Removal Performance of FNA Combinatorial Charge/Hydrophobicity Library Variants. Mutations are Listed According to BPN' Numbering. Performance Index and Charge/Hydrophobicity Changes Calculated Relative to FNA (parent).

| Variant # | Variant | Net Charge Change Relative to FNA | Kyte-Doolitle Hydrophobicity Change relative to FNA | TCA PI | BMI PI |
|---|---|---|---|---|---|
| FNA | S24S-A45A-S101S-N109N-N118N-K213K-L217L | 0 | 0 | 1.00 | 1.00 |
| FH-2 | S24Q-A45Q-S101Q-N109Q-N118Q-K213Q-L217L | −1 | −10.3 | 1.62 | 0.93 |
| FH-3 | S24S-A45Q-S101Q-N109Q-N118Q-K213Q-L217L | −1 | −7.6 | 2.08 | 1.00 |
| FH-4 | S24S-A45A-S101Q-N109Q-N118Q-K213Q-L217L | −1 | −2.3 | 1.46 | 1.01 |
| FH-5 | S24S-A45A-S101S-N109Q-N118Q-K213Q-L217L | −1 | 0.4 | 1.29 | 0.95 |
| FH-6 | S24S-A45A-S101S-N109N-N118Q-K213Q-L217L | −1 | 0.4 | 1.70 | *0.05* |
| FH-7 | S24S-A45A-S101S-N109N-N118N-K213Q-L217L | −1 | 0.4 | 1.95 | 0.95 |
| FH-8 | S24E-A45Q-S101Q-N109Q-N118Q-K213Q-L217L | −2 | −10.3 | 1.55 | 0.90 |
| FH-9 | S24E-A45E-S101Q-N109Q-N118Q-K213Q-L217L | −3 | −10.3 | 1.37 | 0.88 |
| FH-10 | S24E-A45E-S101E-N109Q-N118Q-K213Q-L217L | −4 | −10.3 | 1.52 | 0.68 |
| FH-11 | S24E-A45E-S101E-N109E-N118Q-K213Q-L217L | −5 | −10.3 | 2.72 | 0.81 |
| FH-12 | S24E-A45E-S101E-N109E-N118E-K213Q-L217L | −6 | −10.3 | 1.55 | 0.56 |
| FH-13 | S24E-A45E-S101E-N109E-N118E-K213E-L217L | −7 | −10.3 | 1.56 | 0.42 |
| FH-14 | S24L-A45Q-S101Q-N109Q-N118Q-K213Q-L217L | −1 | −3 | 1.27 | 1.02 |
| FH-15 | S24L-A45L-S101Q-N109Q-N118Q-K213Q-L217L | −1 | 4.3 | 1.68 | 0.98 |
| FH-16 | S24L-A45L-S101L-N109Q-N118Q-K213Q-L217L | −1 | 11.6 | 1.47 | 0.94 |
| FH-17 | S24L-A45L-S101L-N109L-N118Q-K213Q-L217L | −1 | 18.9 | 1.17 | 0.89 |
| FH-18 | S24L-A45L-S101L-N109L-N118L-K213Q-L217L | −1 | 26.2 | 1.11 | 0.23 |
| FH-19 | S24L-A45L-S101L-N109L-N118L-K213L-L217L | −1 | 33.5 | 1.19 | 0.20 |
| FH-20 | S24R-A45Q-S101Q-N109Q-N118Q-K213Q-L217L | 0 | −11.3 | 1.31 | 1.01 |
| FH-21 | S24R-A45R-S101Q-N109Q-N118Q-K213Q-L217L | 1 | −12.3 | 1.29 | 0.75 |
| FH-22 | S24R-A45R-S101R-N109Q-N118Q-K213Q-L217L | 2 | −13.3 | 1.28 | 0.46 |
| FH-23 | S24R-A45R-S101R-N109R-N118Q-K213Q-L217L | 3 | −14.3 | 1.21 | 0.33 |
| FH-24 | S24R-A45R-S101R-N109R-N118R-K213Q-L217L | 4 | −15.3 | 1.11 | 0.28 |
| FH-25 | S24R-A45R-S101R-N109R-N118R-K213R-L217L | 5 | −16.3 | 0.98 | 0.23 |
| FH-26 | S24E-A45R-S101R-N109R-N118R-K213R-L217L | 3 | −15.3 | 1.22 | 0.37 |

TABLE 4-2-continued

Relative Expression and Stain Removal Performance of
FNA Combinatorial Charge/Hydrophobicity Library Variants.
Mutations are Listed According to BPN' Numbering.
Performance Index and Charge/Hydrophobicity Changes
Calculated Relative to FNA (parent).

| Variant # | Variant | Net Charge Change Relative to FNA | Kyte-Doolitle Hydrophobicity Change relative to FNA | TCA PI | BMI PI |
|---|---|---|---|---|---|
| FH-27 | S24E-A45E-S101R-N109R-N118R-K213R-L217L | 1 | −14.3 | 1.23 | 0.65 |
| FH-28 | S24E-A45E-S101E-N109R-N118R-K213R-L217L | −1 | −13.3 | 1.55 | 0.89 |
| FH-29 | S24E-A45E-S101E-N109E-N118R-K213R-L217L | −3 | −12.3 | 1.56 | 0.84 |
| FH-30 | S24E-A45E-S101E-N109E-N118E-K213R-L217L | −5 | −11.3 | 1.48 | 0.82 |
| FH-31 | S24E-A45E-S101E-N109E-N118E-K213E-L217L | −7 | −10.3 | 2.89 | 0.65 |
| FH-32 | S24Q-A45Q-S101Q-N109Q-N118Q-K213Q-L217Q | −1 | −17.6 | 1.55 | 1.07 |
| FH-33 | S24Q-A45Q-S101Q-N109Q-N118Q-K213Q-L217E | −2 | −17.6 | 1.68 | 1.07 |

All patents and publications mentioned in the specification are indicative of the levels of those skilled in the art to which the invention pertains. Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by herein. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not excised material is specifically recited herein.

---

We claim:

1. An isolated subtilisin protease variant of a parent *Bacillus* subtilisin, wherein said subtilisin variant is a mature form having proteolytic activity and comprising a substitution at two or more positions selected from positions 24, 45, 101, 109, 118, 213 and 217, wherein said positions wherein the positions are numbered by correspondence with the amino acid sequence of *B. amyloliquefaciens* subtilisin BPN' set forth as SEQ ID NO: 1, and wherein said parent has the sequence of SEQ ID NO: 4 or SEQ ID NO: 7.

2. The isolated subtilisin variant of claim 1, wherein said subtilisin variant has a relative protein expression level performance index (TCA PI) and/or a stain removal activity performance index (BMI PI) that is greater or equal to 0.5.

3. The isolated subtilisin variant of claim 1, wherein said *Bacillus* subtilisin is GG36, and wherein said substitution at two or more positions is selected from: S24Q, S24E, S24L, S24R, R45Q, R45E, R45L, S101Q, S101E, S101L, S101R, Q109E, Q109L, Q109 R, G118Q, G118E, G118L, G118R, T213Q, T213L, T213R, T213E, L217Q, and L217E, wherein the positions correspond to the positions of BPN' subtilisin of SEQ ID NO: 1.

4. The isolated subtilisin variant of claim 1, wherein said *Bacillus* subtilisin is FNA, and wherein said substitution at two or more positions is selected from: S24Q, S24E, S24L, S24R, A45Q, A45E, A45L, A45R, S101Q, S101E, S101L, S101R, N109Q, N109E, N109L, N109R, K213Q, K213E, K213L, K213R, L217Q, L217E, wherein the positions correspond to the positions of BPN' subtilisin of SEQ ID NO: 1.

5. The isolated subtilisin variant of claim 1, wherein said *Bacillus* subtilisin is GG36, and wherein said substitution at two or more positions is selected from S24Q-R45Q-S101Q-G118Q-T213Q, R45Q-S101Q-G118Q-T213Q, S101Q-G118Q-T213Q, G118Q-T213Q, S24E-R45Q-S101Q-G118Q-T213Q, S24E-R45E-S101Q-G118Q-T213Q, S24E-R45E-S101E-G118Q-T213Q, S24E-R45E-S101E-Q109E-G118Q-T213Q, S24E-R45E-S101E-Q109E-G118E-T213Q, S24E-R45E-S101E-Q109E-G118E-T213E, S24L-R45Q-S101Q-G118Q-T213Q, S24L-R45L-S101Q-G118Q-T213Q, S24L-R45L-S101L-G118Q-T213Q, S24L-R45L-S101L-Q109L-G118Q-T213Q, S24L-R45L-S101L-Q109L-G118L-T213Q, S24L-R45L-S101L-Q109L-G118L-T213L, S24R-R45Q-S101Q-G118Q-T213Q, S24R-S101Q-G118Q-T213Q, S24R-S101R-G118Q-T213Q, S24R-S101R-Q109R-G118Q-T213Q, S24R-S101R-Q109R-G118R-T213Q, S24R-S101R-Q109R-G118R-T213R, S24E-S101R-Q109R-G118R-T213R, S24E-R45E-S101R-Q109R-G118R-T213R, S24E-R45E-S101E-Q109R-G118R-T213R, S24E-R45E-S101E-Q109E-G118R-T213R, S24E-R45E-S101E-Q109E-G118E-T213R, S24E-R45E-S101E-Q109E-G118E-T213E, S24Q-R45Q-S101Q-G118Q-T213Q-L217Q, and S24Q-R45Q-S101Q-G118Q-T213Q-L217E, wherein the positions correspond to the positions of BPN' subtilisin of SEQ ID NO: 1.

6. An isolated subtilisin protease variant of the *Bacillus* subtilisin GG36, wherein said subtilisin variant is a mature form having proteolytic activity and comprising the substitution T213Q, wherein said position corresponds to the amino acid sequence of *B. amyloliquefaciens* subtilisin BPN' set forth as SEQ ID NO: 1.

7. The isolated subtilisin variant of claim 1, wherein said *Bacillus* subtilisin is FNA, and wherein said substitution at two or more positions is selected from S24Q-A45Q-S101Q-N109Q-N118Q-K213Q, A45Q-S101Q-N109Q-N118Q-K213Q, S101Q-N109Q-N118Q-K213Q, N109Q-N118Q-K213Q, N118Q-K213Q, S24E-A45Q-S101Q-N109Q-N118Q-K213Q, S24E-A45E-S101Q-N109Q-N118Q-K213Q, S24E-A45E-S101E-N109Q-N118Q-K213Q, S24E-A45E-S101E-N109E-N118Q-K213Q, S24E-A45E-S101E-N109E-N118E-K213Q, S24E-A45E-S101E-N109E-N118E-K213E, S24L-A45Q-S101Q-N109Q-N118Q-K213Q, S24L-A45L-S101Q-N109Q-N118Q-K213Q, S24L-A45L-S101L-N109Q-N118Q-K213Q, S24L-A45L-S101L-N109L-N118Q-K213Q, S24L-A45L-S101L-N109L-N118L-K213Q, S24L-A45L-S101L-N109L-N118L-K213L, S24R-A45Q-S101Q-N109Q-N118Q-K213Q, S24R-A45R-S101Q-N109Q-N118Q-K213Q, S24R-A45R-S101R-N109Q-N118Q-K213Q, S24R-A45R-S101R-N109R-N118Q-K213Q, S24R-A45R-S101R-N109R-N118R-K213Q, S24R-A45R-S101R-N109R-N118R-K213R, S24E-A45R-S101R-N109R-N118R-K213R, S24E-A45E-S101R-N109R-N118R-K213R, S24E-A45E-S101E-N109R-N118R-K213R, S24E-A45E-S101E-N109E-N118R-K213R, S24E-A45E-S101E-N109E-N118E-K213R, S24E-A45E-S101E-N109E-N118E-K213E, S24Q-A45Q-S101Q-N109Q-N118Q-K213Q-L217Q, and S24Q-A45Q-S101Q-N109Q-N118Q-K213Q-L217E, wherein the positions correspond to the positions of BPN' subtilisin of SEQ ID NO: 1.

8. The isolated subtilisin variant of claim 1, wherein said variant has proteolytic activity and comprises the substitution K213Q, wherein said position is numbered by correspondence with the amino acid sequence of *B. amyloliquefaciens* subtilisin BPN' set forth as SEQ ID NO: 1.

9. A cleaning composition comprising at least one subtilisin variant of claim 1.

10. The cleaning composition of claim 9, wherein said cleaning composition is a detergent.

11. The cleaning composition of claim 10, wherein said detergent is a heavy duty liquid or dry laundry detergent.

12. The cleaning composition of claim 10, wherein said detergent is a dish detergent.

13. The cleaning composition of claim 9, further comprising one or more additional enzymes or enzyme derivatives selected from hemicellulases, cellulases, peroxidases, proteases, metalloproteases, xylanases, lipases, phospholipases, esterases, perhydrolasess, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

14. The cleaning composition of claim 13, further comprising at least one stabilizing agent.

15. A cleaning composition comprising at least 0.0001 weight percent of at least one subtilisin variant of claim 1, and optionally, at least one suitable adjunct ingredient.

* * * * *

SEQUENCE LISTING

```
<160> NUMBER OF SEQ ID NOS: 11

<210> SEQ ID NO 1
<211> LENGTH: 275
<212> TYPE: PRT
<213> ORGANISM: B. amyloliquefaciens

<400> SEQUENCE: 1

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125
```

```
Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Tyr Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 2
<211> LENGTH: 1303
<212> TYPE: DNA
<213> ORGANISM: Artificial Sequence
<220> FEATURE:
<223> OTHER INFORMATION: Chemically synthesized oligonucleotide used in
      GG36 protease production

<400> SEQUENCE: 2
atctcaaaaa aatgggtcta ctaaaatatt actccatcta ttataataaa ttcacagaat      60
agtcttttaa gtaagtctac tctgattttt tttaaaagga gagggtaaag agtgagaagc     120
aaaaaattgt ggatcgtcgc gtcgaccgca ttgctgattt ctgttgcttt tagctcatcc     180
atcgcatccg ctgctgaaga agcaaaagaa aaatatttaa ttggctttaa tgagcaggaa     240
gctgtcagtg agtttgtaga acaagttgag gcaaatgacg aggtagccat tctctctgag     300
gaagaggaag tcgaaattga attgcttcat gaatttgaaa cgattcctgt tctgtccgtt     360
gagttaagcc cagaagatgt ggacgcgtta gagctcgatc agctatttc ttatattgaa      420 gaggatgcag aagtaactac aatggcgcaa tcggtaccat ggggaattag cagagtacaa     480
gccccagctg cacataaccg tggattgaca ggttctggtg taaaagttgc tgtccttgat     540
accggtattt ccactcatcc agacttaaat attcgtggtg gagctagctt tgtaccaggg     600
gaaccatcca ctcaagatgg caatggacat ggcactcatg ttgccggcac aatcgcggct     660
cttaacaatt caattggtgt tcttggcgta gcgccaagcg cagaactata cgctgttaaa     720
gtattaggag caagcggttc aggctctgtc agctctattg cccaaggatt ggaatgggca     780
gggaacaatg gcatgcacgt tgctaatctt agtttaggat ctccttcgcc aagtgccaca     840
cttgagcaag ctgttaatag cgcgacttct agaggcgttc ttgttgtagc ggcctctgga     900
aattcaggtg caggctcaat cagctatccg gcccgttatg cgaacgctat ggcagtcgga     960
gctactgacc aaaacaacaa ccgcgccagc ttttcacagt atggcgcagg gcttgacatt    1020
gtcgcaccag gtaaacgt gcagagcact tacccaggtt caacatatgc cagcttaaac      1080
ggtacatcaa tggctactcc tcatgttgca ggtgcggctg cacttgttaa acaaaagaac    1140
```

-continued

```
ccatcttggt ccaatgtaca aatccgcaat catcttaaga atacggcaac tagcttagga    1200
agcacaaact tgtatggaag cggacttgtc aatgcagaag ctgcaactcg ttaaaagctt    1260
aactcgagat aaaaaaccgg ccttggcccc gccggttttt tat                      1303
```

<210> SEQ ID NO 3
<211> LENGTH: 380
<212> TYPE: PRT
<213> ORGANISM: Artificial Sequence
<220> FEATURE:
<223> OTHER INFORMATION: Chemically synthesized GG36 precursor protein

<400> SEQUENCE: 3

```
Met Arg Ser Lys Lys Leu Trp Ile Val Ala Ser Thr Ala Leu Leu Ile
1               5                   10                  15

Ser Val Ala Phe Ser Ser Ile Ala Ser Ala Glu Glu Ala Lys
            20                  25                  30

Glu Lys Tyr Leu Ile Gly Phe Asn Glu Gln Glu Ala Val Ser Glu Phe
            35                  40                  45

Val Glu Gln Val Glu Ala Asn Asp Glu Val Ala Ile Leu Ser Glu Glu
        50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Ala Leu Val Lys Gln Lys Asn Pro Ser Trp Ser Asn Val Gln Ile Arg
```

```
                    340                 345                 350
Asn His Leu Lys Asn Thr Ala Thr Ser Leu Gly Ser Thr Asn Leu Tyr
            355                 360                 365

Gly Ser Gly Leu Val Asn Ala Glu Ala Ala Thr Arg
    370                 375                 380

<210> SEQ ID NO 4
<211> LENGTH: 269
<212> TYPE: PRT
<213> ORGANISM: Artificial sequence
<220> FEATURE:
<223> OTHER INFORMATION: Chemically synthesized mature GG36 protease

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 5
<211> LENGTH: 1309
<212> TYPE: DNA
<213> ORGANISM: Artificial Sequence
<220> FEATURE:
<223> OTHER INFORMATION: Chemically synthesized oligonucleotide used in
      FNA protease production

<400> SEQUENCE: 5
```

```
gaattcatct caaaaaaatg ggtctactaa aatattattc catctattat aataaattca    60
cagaatagtc ttttaagtaa gtctactctg aattttttta aaaggagagg gtaaagagtg   120
agaagcaaaa aattgtggat cagtttgctg tttgctttag cgttaatctt tacgatggcg   180
ttcggcagca catccagcgc gcaggctgca gggaaatcaa acggggaaaa gaaatatatt   240
gtcgggttta aacagacaat gagcacgatg agcgccgcta agaagaaaga cgtcatttct   300
gaaaaaggcg ggaaagtgca aaagcaattc aaatatgtag acgcagctag cgctacatta   360
aacgaaaaag ctgtaaaaga attgaaaaaa gacccgagcg tcgcttacgt tgaagaagat   420
cacgtagcac acgcgtacgc gcagtccgtg ccatatggcg tatcacaaat taaagccccct   480 gctctgcact ctcaaggcta caccggttca aatgttaaag tagcggttat cgacagcggt   540
atcgattctt ctcatccaga tcttaaagta gcaggcggag ccagcatggt tccttctgaa   600
acaaatcctt tccaagacaa caactctcac ggaacacacg ttgctggtac cgttgcggct   660
cttaataact caatcggtgt attaggcgtt gcgccaagcg catcacttta cgctgtaaaa   720
gttctcggcg ccgacggttc cggccaatac agctggatca ttaacggaat cgagtgggcg   780
atcgcaaaca atatggacgt tattaacatg agcctcggcg gaccgtccgg ttctgctgct   840
ttaaaagcgg cagttgataa agccgttgca tccggcgtcg tagtcgttgc ggcagccggc   900
aacgaaggca cttccggcag ctcaagcaca gtgggctacc ctggtaaata cccttctgtc   960
attgcagtag gcgctgtcga cagcagcaac caaagagcat ctttctcaag cgtaggacct  1020
gagctcgatg tcatggcacc tggcgtatct atccaaagca cgcttcctgg aaacaaatac  1080
ggcgcgttga acggtacatc aatggcatct ccgcacgttg ccggagccgc ggctttgatt  1140
ctttctaagc acccgaactg gacaaacact caagtccgca gctctctaga aaacaccact  1200
acaaaacttg gtgattcttt ctactatgga aaagggctga tcaatgtaca ggcggcagct  1260 cagtaaaaact cgagataaaa aaccggcctt ggccccgccg gttttttat         1309
```

<210> SEQ ID NO 6
<211> LENGTH: 382
<212> TYPE: PRT
<213> ORGANISM: Artificial Sequence
<220> FEATURE:
<223> OTHER INFORMATION: Chemically synthesized FNA precursor protein

<400> SEQUENCE: 6

```
Met Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140
```

```
Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
            165                 170                 175

Gly Thr Val Ala Ala Leu Asn Asn Ser Ile Gly Val Leu Gly Val Ala
        180                 185                 190

Pro Ser Ala Ser Leu Tyr Ala Val Lys Val Leu Gly Ala Asp Gly Ser
    195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
            245                 250                 255

Val Ala Ala Ala Gly Asn Glu Gly Thr Ser Gly Ser Ser Ser Thr Val
        260                 265                 270

Gly Tyr Pro Gly Lys Tyr Pro Ser Val Ile Ala Val Gly Ala Val Asp
    275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Leu Asn Gly Thr Ser Met Ala Ser Pro His Val Ala Gly
            325                 330                 335

Ala Ala Ala Leu Ile Leu Ser Lys His Pro Asn Trp Thr Asn Thr Gln
        340                 345                 350

Val Arg Ser Ser Leu Glu Asn Thr Thr Thr Lys Leu Gly Asp Ser Phe
    355                 360                 365

Tyr Tyr Gly Lys Gly Leu Ile Asn Val Gln Ala Ala Ala Gln
    370                 375                 380

<210> SEQ ID NO 7
<211> LENGTH: 275
<212> TYPE: PRT
<213> ORGANISM: Artificial Sequence
<220> FEATURE:
<223> OTHER INFORMATION: Chemically synthesized mature FNA protease

<400> SEQUENCE: 7

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
            85                  90                  95

Gly Ala Asp Gly Ser Gly Gln Tyr Ser Trp Ile Ile Asn Gly Ile Glu
        100                 105                 110

Trp Ala Ile Ala Asn Asn Met Asp Val Ile Asn Met Ser Leu Gly Gly
    115                 120                 125
```

```
Pro Ser Gly Ser Ala Ala Leu Lys Ala Ala Val Asp Lys Ala Val Ala
        130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
        210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide motif

<400> SEQUENCE: 8

His Gly Thr His
1

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide motif
<220> FEATURE:
<221> NAME/KEY: misc_feature
<222> LOCATION: (6)..(6)
<223> OTHER INFORMATION: Xaa can be any naturally occurring amino acid

<400> SEQUENCE: 9

Gly Thr Ser Met Ala Xaa Pro
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide motif

<400> SEQUENCE: 10

His Gly Thr Arg
1

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide motif
```

```
<220> FEATURE:
<221> NAME/KEY: misc_feature
<222> LOCATION: (4)..(4)
<223> OTHER INFORMATION: Xaa is Ala or Val
<220> FEATURE:
<221> NAME/KEY: misc_feature
<222> LOCATION: (5)..(5)
<223> OTHER INFORMATION: Xaa is Ala or Ser

<400> SEQUENCE: 11

Gly Thr Ser Xaa Xaa Pro
1               5
```